(12) United States Patent
Dansereau et al.

(10) Patent No.: US 10,278,930 B2
(45) Date of Patent: May 7, 2019

(54) METHOD FOR RELIEVING SINUS CONGESTION

(71) Applicant: The Procter & Gamble Company, Cincinnati, OH (US)

(72) Inventors: Richard John Dansereau, Cincinnati, OH (US); Daren Anness, Loveland, OH (US); Guhan Balan, Cincinnati, OH (US); David Ramsey, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 97 days.

(21) Appl. No.: 15/460,459

(22) Filed: Mar. 16, 2017

(65) Prior Publication Data

US 2018/0263932 A1 Sep. 20, 2018

(51) Int. Cl.
*A61K 9/50* (2006.01)
*A61K 31/137* (2006.01)

(52) U.S. Cl.
CPC .......... *A61K 31/137* (2013.01); *A61K 9/5078* (2013.01); *A61K 9/5084* (2013.01)

(58) Field of Classification Search
None
See application file for complete search history.

(56) References Cited

U.S. PATENT DOCUMENTS

| | | | |
|---|---|---|---|
| 4,794,001 A | 12/1988 | Mehta et al. | |
| 5,133,974 A | 7/1992 | Paradissis et al. | |
| 5,229,131 A | 7/1993 | Amidon et al. | |
| 5,580,578 A | 12/1996 | Oshlack et al. | |
| 5,834,024 A | 11/1998 | Heinicke et al. | |
| 6,228,398 B1 | 5/2001 | Devane et al. | |
| 6,267,990 B1 | 7/2001 | Fischer et al. | |
| 6,500,457 B1 | 12/2002 | Midha et al. | |
| 6,579,536 B1 | 6/2003 | Hirsch et al. | |
| 6,627,223 B2 | 9/2003 | Percel et al. | |
| 6,663,888 B2 | 12/2003 | Percel et al. | |
| 6,730,321 B2 | 5/2004 | Ting et al. | |
| 7,022,345 B2 | 4/2006 | Valducci | |

(Continued)

FOREIGN PATENT DOCUMENTS

EP 1064938 A1 3/2001
WO WO2007143156 A1 12/2007

(Continued)

OTHER PUBLICATIONS

Fadda, H.M. et al., "Dissolution of pH response formulations in media resembling intestinal fluids: bicarbonate versus phosphate buffers", J. Drug Del. Sci. Tech., 15(4) 273-279, 2005.

(Continued)

*Primary Examiner* — Carlos A Azpuru
*Assistant Examiner* — Casey S Hagopian
(74) *Attorney, Agent, or Firm* — Amanda Herman; Alexandra S. Anoff

(57) ABSTRACT

A method for temporarily relieving sinus congestion and pressure comprising administering to a human a dose of a multi-particle pulsatile oral dosage form with an immediate release form and a plurality of delayed release particles. The immediate release form contains about 10 mg phenylephrine hydrochloride. The delayed release form contains a core with coatings including a phenylephrine coating containing about 10 mg phenylephrine hydrochloride and a pH sensitive coating.

18 Claims, 11 Drawing Sheets

(56) References Cited

U.S. PATENT DOCUMENTS

| | | |
|---|---|---|
| 7,670,627 B2 | 3/2010 | Shefer et al. |
| 7,920,128 B2 | 4/2011 | Park et al. |
| 2002/0192282 A1 | 12/2002 | Beckert et al. |
| 2005/0069580 A1 | 3/2005 | Hirsh et al. |
| 2006/0269605 A1 | 11/2006 | Lizio et al. |
| 2006/0280795 A1 | 12/2006 | Penhasi et al. |
| 2007/0281019 A1 | 12/2007 | Ulloa et al. |
| 2007/0281020 A1 | 12/2007 | Ulloa et al. |
| 2008/0020055 A1 | 1/2008 | Monteith et al. |
| 2008/0311201 A1 | 12/2008 | Der-Yang et al. |
| 2009/0220611 A1 | 9/2009 | Dargelas et al. |
| 2010/0068280 A1 | 3/2010 | Patton |
| 2010/0249237 A1 | 9/2010 | Gelotte et al. |
| 2016/0081948 A1 | 3/2016 | Dansereau |

FOREIGN PATENT DOCUMENTS

| | | |
|---|---|---|
| WO | WO2007143158 A2 | 12/2007 |
| WO | WO2009086941 A1 | 7/2009 |
| WO | WO2010094996 A1 | 8/2010 |
| WO | WO2016044703 A1 | 3/2016 |

OTHER PUBLICATIONS

Office Actions from U.S. Appl. No. 11/756,881, filed Jun. 1, 2007.
Office Actions from U.S. Appl. No. 10/516,950, filed Aug. 11, 2005.
Office Actions from U.S. Appl. No. 14/857,848, filed Sep. 28, 2015.
International Search Report and Written Opinion for PCT/US2015/050894—dated Jan. 5, 2016.
14743 International Search Report and Written Opinion for PCT/US2018/022774 dated Jun. 14, 2018.

METHOD FOR RELIEVING SINUS CONGESTION

FIELD OF THE INVENTION

The present invention is generally related to a method of relieving sinus congestion for at least eight hours by administering a dosage form containing immediate and delayed release phenylephrine particles and more particularly, where the delayed release of phenylephrine is pulsatile.

BACKGROUND OF THE INVENTION

Decongestants are commonly used to relieve nasal congestion and a commonly used decongestant is phenylephrine. Phenylephrine is widely available to consumers as an over-the-counter (OTC) drug.

One problem for immediate release dosage forms containing phenylephrine is that in order for it to be most effective, it must be taken frequently. The current U.S. Monograph for an oral dosage form comprising phenylephrine hydrochloride is ten milligrams every four hours. Consumers find it inconvenient to dose every four hours and frequently miss doses, especially mid-day doses, which can result in poor symptomatic relief.

Furthermore, the short time period between doses makes it difficult to combine phenylephrine with other drug actives, in particular actives that are commonly used in multi-symptom relief cold/flu products, which have longer dosing intervals. Therefore, consumers have to take multiple dosage forms and dose several times a day at various intervals to experience the optimal relief of their cold/flu symptoms.

One of the reasons for frequent dosing is because phenylephrine is subject to high first pass metabolism and a short half-life. Upon oral administration, phenylephrine is rapidly metabolized and is subsequently conjugated into sulfate and glucuronide forms. However, the therapeutic decongestant activity is attributed to the portion of the phenylephrine that is not metabolized and stays as the unconjugated parent active. Accordingly, it is of benefit to maximize the duration of time of the unconjugated active form present in bloodstream after oral administration.

There have been several attempts to modify the release of phenylephrine in order to prolong the dosing interval. Many approaches related to the modified release of phenylephrine focus on dual release mechanisms comprising an immediate release form coupled with an extended first-order or zero-order extended phase of release. A problem with these bi-modal approaches is that during the extended release phase, low levels of unconjugated phenylephrine active are likely to be present in the bloodstream due to rapid first pass metabolism. An alternate approach would be a pulsatile dose form that releases active at different regions in the intestine and can mimic immediate release dosage forms administered every 4 hours. Such a dosage form would be beneficial to the consumer and allow for more effective and convenient dosing.

As such, there remains a need in the area of consumer selected OTC therapies for improved options for the treatment of symptoms associated with the common cold (rhinovirus), influenza, or environmental allergies. In particular, there exists a need for a convenient longer acting phenylephrine dosage form that can provide relief over an extended period of time relative to current therapies.

SUMMARY OF THE INVENTION

A method for temporarily relieving sinus congestion and pressure comprising administering to a human a dose of a multi-particle pulsatile oral dosage form comprising: (a) an immediate release form comprising about 10 mg phenylephrine hydrochloride; and (b) a plurality of delayed release particles wherein each delayed release particle comprises: (i) a core wherein at least about 85% of the cores comprise a diameter from about 500 µm to about 710 µm; (ii) a phenylephrine coating comprising phenylephrine hydrochloride; (iii) a pH sensitive coating comprising an acrylate copolymer selected from the group consisting of methylmethacrylate esters copolymerized with methacrylic acid, acrylic acid and esters copolymerized with methacrylic acid and esters, ammonio-containing acrylate copolymers, and combinations thereof; wherein the pH sensitive coating is from 40 µm to about 80 µm thick; wherein the plurality of delayed release particles comprise about 10 mg phenylephrine hydrochloride.

A method for temporarily relieving sinus congestion and pressure comprising administering to a human a dose of a multi-particle pulsatile oral dosage form comprising: (a) an immediate release form comprising about 10 mg phenylephrine hydrochloride; and (b) a plurality of delayed release particles wherein each delayed release particle comprises: (i) a core; (ii) a phenylephrine coating comprising phenylephrine hydrochloride; (iii) a pH sensitive coating wherein the pH sensitive coating comprises an enteric coating; wherein the pH sensitive coating is from 40 µm to about 80 µm thick; wherein the plurality of delayed release particles comprise from about 7 mg to about 15 mg phenylephrine hydrochloride; wherein the pulsatile dosage form comprises a $C_{max2}$ and an $AUC_{4-8}$ wherein an upper bound of a 90% confidence interval for a ratio of means for the $C_{max2}$ and the $AUC_{4-8}$ of the pulsatile dosage form relative to two sequential doses of an immediate release phenylephrine taken four hours apart is at least 85%.

A method for temporarily relieving sinus congestion and pressure comprising administering to a human a dose of a multi-particle pulsatile oral dosage form comprising: (a) an immediate release form comprising phenylephrine hydrochloride; and (b) a plurality of delayed release particles wherein each delayed release particle comprises: (i) a core; (ii) a phenylephrine coating comprising phenylephrine hydrochloride; (iii) a pH sensitive coating wherein the pH sensitive coating is degradable at a pH from about 6 to about 8; wherein the plurality of delayed release particles comprise from about 7 mg to about 20 mg phenylephrine hydrochloride; wherein the ratio of the amount of phenylephrine in the immediate release form to the amount of phenylephrine in the delayed release form is from about 1.5:1 to about 1:1.5; wherein the pulsatile dosage form comprises an $AUC_{0-4}$ and an $AUC_{4-8}$ wherein a mean $AUC_{0-4}$ and a mean $AUC_{4-8}$ of the pulsatile dosage form meets or exceeds a mean $AUC_{0-4}$ and a mean $AUC_{4-8}$ of two sequential doses of an immediate release phenylephrine taken four hours apart.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
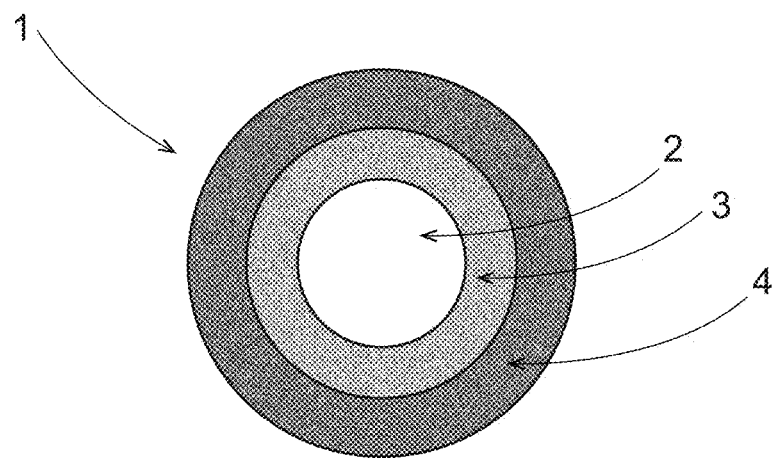
FIG. 1 is a schematic of an immediate release particle.

The present invention relates to a multi-particle, oral dose form designed for an immediate release of phenylephrine hydrochloride (PE) followed by one or more delayed pulses. In one example, one or more delayed pulses are formulated so the phenylephrine is released in a different region of the gastrointestinal tract in order to provide an extended period of congestion relief. In one example, the delayed delivery doses are enteric coated and designed to release the phenylephrine in the distal small intestine. While not wishing to be bound by theory, it is believed that delivery to the distal small intestine is effective because the effects of the operative metabolic enzymes are reduced, ultimately resulting in an optimal amount of unconjugated phenylephrine in the blood and longer duration of dosing. In this way, therapeutic levels of phenylephrine can be delivered at the appropriate dose, intestinal region, and time interval to provide effective relief over an extended period of time.

The multi-particle, solid oral dose form can be a tablet, a sachet, or a capsule, containing phenylephrine which can be administered every 6, 8, or 12 hours to provide extended congestion relief to a patient. In one example, the dose form can meet or exceed the bioavailability and/or bioequivalence as compared to two or three immediate release doses of phenylephrine taken at four hour time intervals.

As used herein, "AUC" refers to the area under the concentration-time curve from time of dosing up to a time point, calculated by the linear trapezoidal rule. AUC is a parameter that shows the cumulative plasma concentration of a drug over time, and is an indicator of the total amount and availability of a drug. "$AUC_{(0-t)}$" is defined as AUC for any value of time up to t hours. In one example, t is 12 hours (referred to herein as $AUC_{(0-12)}$), other examples can include $AUC_{(0-4)}$, and $AUC_{(0-8)}$. "$AUC_{(4-8)}$" refers to AUC between four and eight hours after dosing. "$AUC_{(0-inf)}$" is defined as calculated AUC extrapolated to infinity. $AUC_{(0-inf)}$, is calculated as equal to $AUC_{last}$+Ct/lambda z, wherein $AUC_{last}$ is the AUC until the time point of last measurable concentration, Ct is the last measurable plasma concentration, and lambda z is the terminal phase rate constant. Terminal phase rate constant lambda z is derived from the slope of the drug concentration-time curve using linear regression on terminal data points of the curve.

As used herein, "bioavailability" refers to a rate and extent to which the active drug ingredient or therapeutic moiety is absorbed from a drug product and becomes available for therapeutic action. In one example the drug ingredient can be phenylephrine and it can reach the systemic circulation and can be available at its site of action.

As used herein, "bioequivalent" and "bioequivalency" refers to a dosage form whose rate and extent of absorption do not show a significant difference when administered under similar experimental conditions, to a single dose or multiple doses of a currently available product. Some dosage forms may be equivalent in the extent of their absorption but not in their rate of absorption and yet may be considered bioequivalent because such differences in the rate of absorption are intentional and are reflected in the labeling, are not essential to the attainment of effective body drug concentrations on chronic use, or are considered medically insignificant for the particular drug product studied. A pulsatile PE dose form can meet or exceed the bioequivalence limits of a commercially available, immediate release PE dose taken at 4 hour intervals (reference product). To demonstrate bioequivalence the pulsatile PE dose form (T) is compared to the reference IR product (R) and the 90% confidence intervals for the geometric mean T/R ratios for the parameters, including $C_{max}$, $AUC_{0-last}$ and $AUC_{0-inf}$ fall within the limits of 80.00-125.00%.

As used herein, "conjugated phenylephrine" refers to phenylephrine that is metabolized. This means that the phenylephrine has been conjugated (i.e. chemically altered) by an enzyme. The enzymes which conjugate phenylephrine can include sulfotransferase or UDP-glucuronosyltransferase.

As used herein "delayed release" refers to a particle, a plurality of particles, or a dosage form where the drug active (or actives) are released at a time other than immediately following oral administration. In one example, a delayed release particle, plurality of particles, or dosage form has been deliberately modified such that the majority of the drug active that is contained in or on the particle, plurality of particles, or dosage form is released or absorbed into the blood plasma some period of time after administration. One advantage of a delayed release dosage form is that it can be formulated to release an active after a specified time period or upon encountering the proper environment (for example, release based on pH, enzymatic activity, or solubility). In one example, the delayed release particles have an enteric coating, which means that the particle coatings are pH sensitive and the benefit is not experienced by the user until the particle(s) or dosage form reaches certain regions of the intestine. In one example, a delayed release particle, plurality of particles, or a dosage form can be taken in combination with an immediate release for, which can include an immediate release particle, plurality of particles or other dosage form. In one example, the dosage form or particle(s) do not deliver an active slowly over an extended duration of time, instead the particles can be designed to rapidly or immediately deliver an active after a delay period.

As used herein, "dissolve" refers to disintegrating, dispersing and/or passing into solution.

As used herein, "dose" or "dosage unit" refers to a dosage form containing an amount of a drug active suitable for administration on a single occasion, according to sound medical practice. The dosage form may include a variety of orally administered dosage forms. Non-limiting examples of dosage forms can include particles suspended in a liquid formulation, a solid in a gelatin or foam, or a solid dose in the form of a tablet, powder, granules, pellets, microspheres, nanospheres, beads, or nonpareils, and combinations thereof. In one example, the dosage form is a tablet or a capsule. In another example, the dosage form is a capsule containing delayed release particles and optionally an immediate release form and excipients. Dosage forms can be orally administered and are typically swallowed immediately, slowly dissolved in the mouth, or chewed.

As used herein, "extended release" (ER) refers to a particle, a plurality of particles, or a dosage unit that allows a reduction in dosing frequency as compared to that presented by a conventional dosage form, e.g., a solution or an immediate release dosage form. In one example, an extended release dosage form can be deliberately modified wherein the particle, plurality of particles, or dosage form is formulated in such a manner as to make the drug active available over an extended period of time following administration. One example of an extended release particle, plurality of particles or dosage form is a delayed release (DR) dosage form. Another example of an extended release particle, plurality of particles or dosage form can be pulsatile release dosage forms or particle(s).

As used herein, "immediate release" (IR) refers to a particle, a plurality of particles, or a dosage form wherein no deliberate effort has been made to modify the release rate and in the case of capsules, tablets, and particles the inclusion of a disintegrating agent is not interpreted as a modification.

As used herein, "PK profile" refers to a pharmacokinetic profile which is the concentration of a drug, such as unconjugated phenylephrine, in plasma over time.

As used herein, "pulsatile release" refers to the phenylephrine being released at two or more distinct time periods following ingestion. In one example, the dosage form can have an immediate release form, which can be a plurality of immediate release particles, and a plurality of delayed release particles which results in an immediate release of the first pulse of phenylephrine after administration of the dosage form to the user and a second pulse when the delayed release particles enter the higher pH environment of the small intestine.

As used herein, the term "substantially equivalent" refers to within about 60% of the reference treatment (e.g. ratio of means are ≥60%), in another example within about 70%, in another example within about 75%, in another example within about 80%, in another example within about 85%, in another within about 90%, in another example within about 93%, in another example within about 95%, in another example within about 98%, in another example within about 102%, in another example within about 105%, in another example within about 107%, in another example within about 110%, in another example within about 115%, in another example within about 120%, in another example within about 125%, in another example within about 130%, and in another example within about 140%. Substantially equivalent can refer to, but is not limited to, the PK profile, $C_{max}$, $C_{max1}$, $C_{max2}$, and AUC including $AUC_{0-4}$ and $AUC_{4-8}$.

As used herein, the term "total phenylephrine" refers to the amount of conjugated phenylephrine and unconjugated phenylephrine.

As used herein, the term "treat" or "treating" includes preventing, alleviating, ameliorating, inhibiting, or mitigating one or more health conditions in a mammal. Non-limiting examples of health conditions can include respiratory conditions.

As used herein, "unconjugated phenylephrine" refers to phenylephrine that is unmetabolized and is the therapeutically active form of phenylephrine. Unmetabolized phenylephrine is phenylephrine that has entered the body of the user and is not chemically altered at the time of absorption into the blood plasma or later.

As used herein, the articles "a" and "an" are understood to mean one or more of the material that is claimed or described, for example, " an acrylic acid ester co-polymer" or "a multi-particle dosage form".

All percentages, parts and ratios as used herein are by weight of the dosage form, unless otherwise specified. All such weights as they pertain to listed ingredients are based on the active level and, therefore do not include solvents or by-products that may be included in commercially available materials, unless otherwise specified.

The dosage form, process and methods of the present invention can contain, consist of, or consist essentially of, the essential elements and limitations of the invention described herein, as well as any additional or optional ingredients, components, or limitations described herein or otherwise useful in dosage forms intended for use or consumption by humans.

FIG. 1 shows a schematic of an immediate release particle 1. Immediate release particle 1 can comprise a core 2, a phenylephrine coating 3, and optionally a separation coating 4. In one example, the phenylephrine coating 3 can dissolve or start to dissolve after it reaches the stomach. An optional anti-caking coating can be added to immediate release particles and is not shown in FIG. 1.

Figure 2:
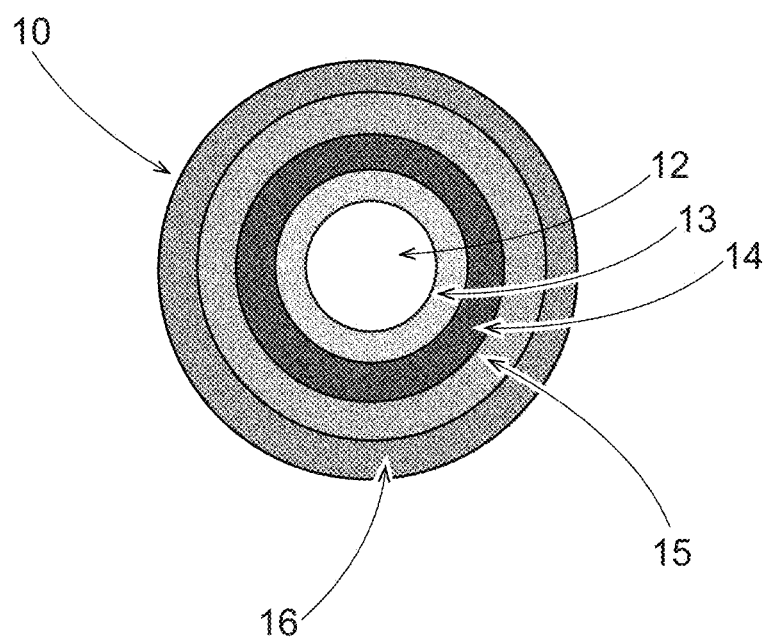
FIG. 2 is a schematic of a delayed release particle.

FIG. 2 shows a schematic of a delayed release particle 10. Delayed release particle 10 comprises a core 12, phenylephrine coating 13, optionally separation coating 14, pH sensitive coating 15, and optionally anti-caking coating 16.

In one example, the immediate release particles and/or the delayed release particles can have a separation coating. For immediate release particles the separation coating can help limit friability in handling the particles. Additionally, for delayed release particles the separation coating can separate the highly soluble phenylephrine layer from the pH sensitive coating. If phenylephrine leaches or migrates into the pH sensitive coating then this may result in premature drug dissolution. Non-limiting examples of separation coatings can include talc, polyvinyl alcohol-polyethylene glycol graft co-polymer (commercially available as Kollicoat® IR, from BASF, Tarrytown, N.J.), hydroxypropyly methylcellulose, hydroxypropyl cellulsoe, polyvinylpyrrolidine, and combinations thereof. In another example, the separation coating can be a pH independent polymer. In another example, the separation coating can be a pH independent polymer. In one example, the separation coating can contain polyvinyl alcohol.

In one example, the anti-caking coating can be sprayed onto the delayed release particles to prevent the particles from sticking together during storage. In another example, the immediate release particles can have an anti-caking coating. If the particles stick together, this can cause uneven dissolution, which alters the carefully timed release of the phenylephrine. The anti-caking coating can be any material that prevents the particles from sticking together. In one example, the anti-caking coating can be clear and in another example the anti-caking coating can be translucent. In another example, the anti-caking coating can be opaque. In another example, the anti-caking coating can be a white powder. In another example, the anti-caking coating can contain a color. In one example, the anti-caking coating can contain a fine particulate that has a high relatively high surface area and is insoluble in water. In one example the surfaces area is greater than about 100 $m^2/g$, in another example greater than about 150 m²/g, in another example greater than about 175 m²/g, and in another example greater than about 200 m²/g. In one example, the weight percent (wt. %) increase of the particle after the anti-caking coating is added can be from about 0.1% to about 5%, in another example from about 0.15% to about 3%, and in another example from about 0.2% to about 2%.

Non-limiting examples of anti-caking coatings can include talc, sodium ferrocyanide, potassium ferrocyanide, calcium carbonate, magnesium carbonate, silicon dioxide, hydrophilic fumed silica (commercially available as Aerosil® 200, Evonik Industries, Parsippany, N.J.), precipitated silica, sodium aluminosilicate, and combinations thereof. In one example, the anti-caking coating contains hydrophilic fumed silica. In another example, the anti-caking coating can contain a thin aqueous coating based on glycerol monostearate and/or hydroxypropyl methylcellulose. In another example, the anti-caking coating can contain polyvinyl alcohol, and/or polyvinyl alcohol-polyethylene glycol graft copolymer (commercially available as Kollicoat® IR, BASF, Tarrytown, N.J.).

Owing to the different pH environments and variability within the GI tract, it can be difficult to predict the level and type of polymer required to affect the desired pulsed release characteristics. In one example, of a pulsed release phenylephrine dosage form, the polymer type, coating level, particle population ratios, and individual dose levels are carefully selected and tailored based on dissolution and pharmacokinetic parameters to achieve a dosage form with a PK profile that meets or exceeds bioequivalence limits and/or bioavailability and/or is substantially equivalent relative to sequentially dosed immediate release forms of phenylephrine taken at regular, usually four hour, intervals.

An example, may include a mixture of immediate release forms and delayed release particles at dosages that are not bioequivalent to sequentially dosed immediate release forms but can nevertheless be registered in the US and other geographies through appropriately designed clinical pharmacokinetic, safety and/or efficacy trials or additional supporting data. Another example can include a mixture of immediate release and delayed release particles at dosages that are substantially bioequivalent to two or three sequentially dosed immediate released dosage forms.

The PK profile examines the time course in vivo after phenylephrine has been administered and includes the $C_{max}$, AUC, $t_{lag}$, and $t_{max}$. $C_{max}$ is the maximal plasma concentration observed. $t_{max}$ is the time to reach $C_{max}$, $t_{lag}$ is the lag time prior to the first quantifiable plasma concentration level. Other parameters of interest can include partial area under the curves including $AUC_{(0-4)}$ and $AUC_{(4-8)}$; plasma concentration values at 4 and 8 hours post-dose ($C_{4hr}$ and $C_{8hr}$); $C_{max}$ which refers to the maximum plasma concentration over the entire dosing interval; $C_{max1}$ which refers to the maximum plasma concentration that occurs between 0 and 2 hours after dosing; and $C_{max2}$ which refers to the maximum plasma concentration that occurs between 2 and 12 hours after dosing.

Example 1

Figure 3:
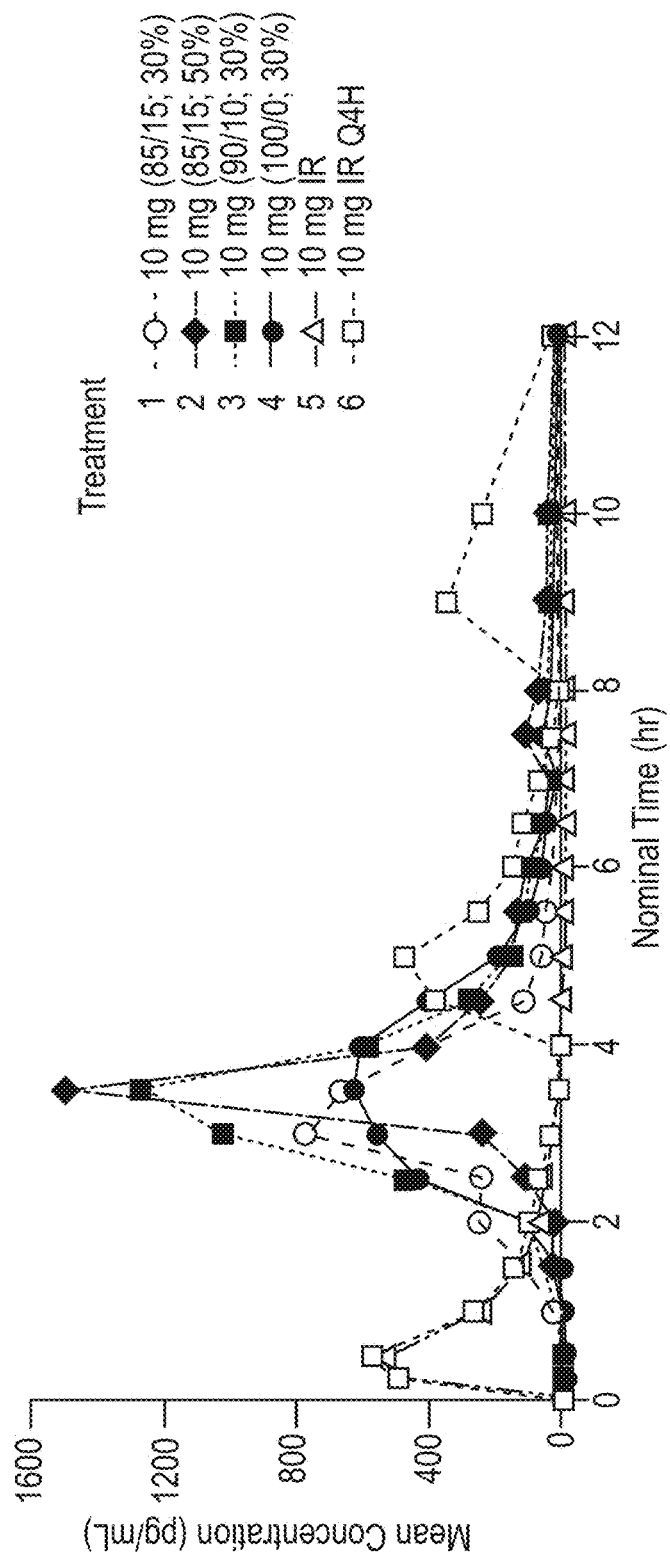
FIG. 3 shows the mean concentration of unconjugated phenylephrine, in vivo over time for different formulation prototypes.
Figure 4:
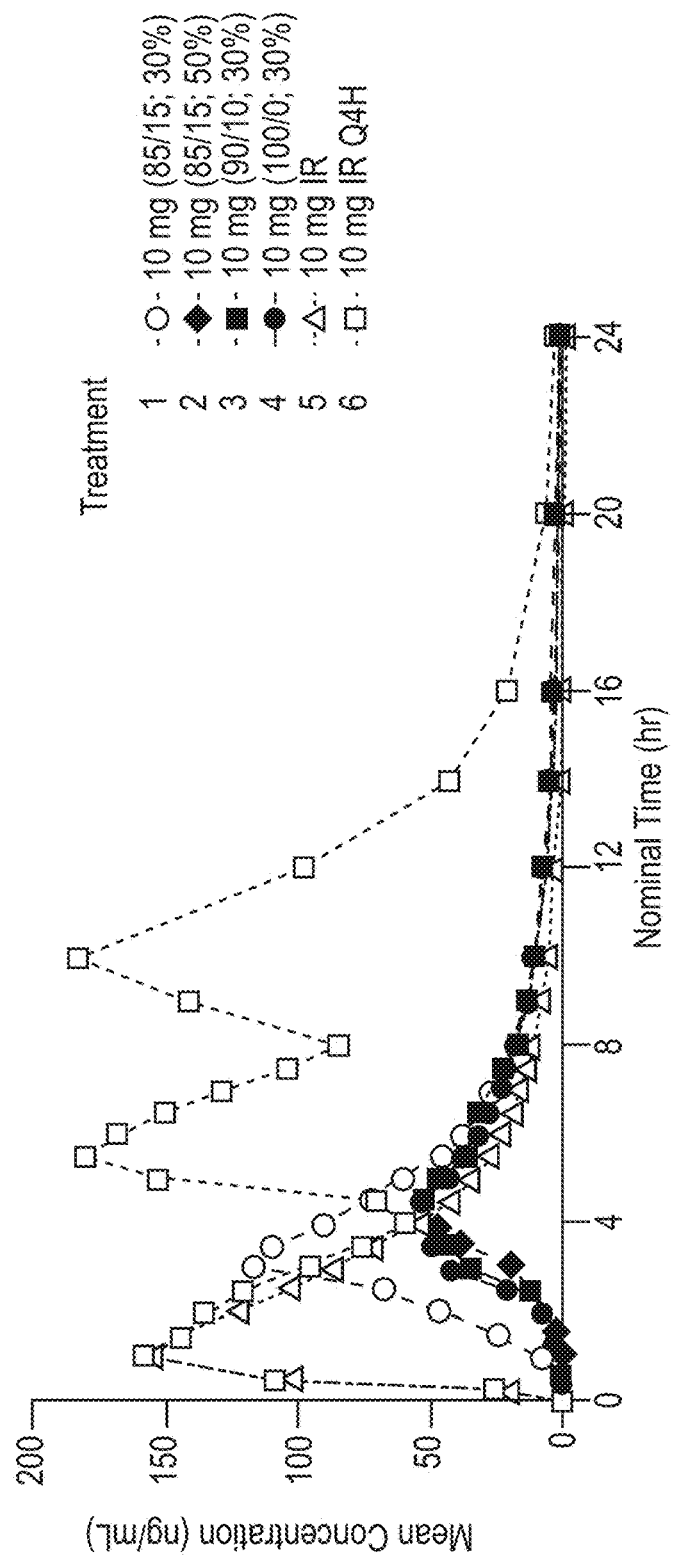
FIG. 4 shows the mean concentration of total phenylephrine, in vivo over time for different formulation prototypes.

PK parameters for unconjugated and total PE from an in vivo study that evaluated four delayed release treatments to a commercially available phenylephrine product are shown in Table 1 and Table 2 and FIGS. 3 and 4. Treatments 1-6 are further described in Table 10, hereafter. Treatments 5 and 6 used a commercially available phenylephrine product, Equate® Non-Drowsy Suphedrine PE (Batch No. 1DE1383). Treatment 5 was administered once at t=0 hours. Treatment 6 was administered three times, once at t=0, once at t=4, and then again at t=8.

Table 1, which is detailed below, shows a summary of the key PK parameters in vivo, $C_{max}$, $AUC_{last}$, $t_{lag}$, and $t_{max}$, for unconjugated PE.

TABLE 1

| Treatment | $C_{max}$ (pg/mL) | $AUC_{last}$ (pg · hr/mL) | $t_{lag}$ (h) | $t_{max}$ (h) |
| --- | --- | --- | --- | --- |
| 1 | 1294 (75.4) | 1481 (83.4) | 1 (0.5, 2.5) | 3 (2, 4) |
| 2 | 1728 (95.4) | 1872 (57.8) | 2.5 (1, 3.5) | 3.5 (1.5, 8) |
| 3 | 1978 (77.9) | 2325 (60.8) | 2.5 (0.3, 4.5) | 3.5 (2.5, 5.5) |
| 4 | 1444 (64.5) | 1824 (41.5) | 2 (1, 3) | 3.25 (2.5, 4) |
| 5 | 689 (54.4) | 632 (21.0) | 0 (0, 0) | 0.5 (0.25, 0.53) |
| 6 | 798 (33.4) | 2210 (20.9) | 0 (0, 0) | 0.5 (0.25, 1)* |

Mean (CV %) for $C_{max}$, AUC and Median (range) for $t_{lag}$ and $t_{max}$
*For Treatment 6, $t_{max}$ values displayed are corrected for dosing time Table 2, which is detailed below, shows a summary of the key PK parameters in vivo, $C_{max}$, $AUC_{last}$, $t_{lag}$, $t_{max}$ for total PE.

TABLE 2

| Treatment | $C_{max}$ (ng/mL) | $AUC_{last}$ (ng · hr/mL) | Ratio of $AUC_{last}$ of unconjugated to $AUC_{last}$ total phenylephrine | $t_{lag}$ (h) | $t_{max}$ (h) |
| --- | --- | --- | --- | --- | --- |
| 1 | 139 (29.6) | 479 (22.1) | 0.003 (103.9) | 0.5 (0.25, 0.5) | 3 (2, 5) |
| 2 | 63 (50.0) | 269 (38.3) | 0.008 (72.6) | 2 (1, 3) | 4 (2, 8) |
| 3 | 73 (41.1) | 303 (26.1) | 0.008 (73.0) | 0.5 (0.25, 0.5) | 4 (3, 6.5) |
| 4 | 75 (54.4) | 323 (33.5) | 0.006 (52.4) | 0.358 (0.25, 0.5) | 4 (2.5, 5.5) |

TABLE 2-continued

| Treatment | $C_{max}$ (ng/mL) | $AUC_{last}$ (ng · hr/mL) | Ratio of $AUC_{last}$ of unconjugated to $AUC_{last}$ total phenylephrine | $t_{lag}$ (h) | $t_{max}$ (h) |
|---|---|---|---|---|---|
| 5 | 163 (20.7) | 570 (15.6) | 0.001 (30.4) | 0 (0, 0) | 1 (0.5, 2.0) |
| 6 | 206 (17.2) | 1795 (22.7) | 0.001 (22.2) | 0 (0, 0) | 1.5 (1, 2.5) |

Mean (CV %) for $C_{max}$, AUC, and ratio and Median (range) for $t_{lag}$ and $t_{max}$
*For Treatment 6, $t_{max}$ values displayed are corrected for dosing time.

FIG. 3 shows the mean concentration of unconjugated phenylephrine over time for different treatments. One example of a desired treatment can be one where the second pulse has a substantially equivalent $C_{max}$, $AUC_{last}$, $t_{lag}$, $t_{max}$ to Treatment 6. FIG. 4 shows the mean concentration of total phenylephrine over time for different treatments. One example of a desired treatment can be one where the second pulse has a substantially equivalent $C_{max}$, $AUC_{last}$, $t_{lag}$, $t_{max}$ to Treatment 6.

The treatments demonstrate that the ratio of $AUC_{last}$ unconjugated to $AUC_{last}$ of total phenylephrine is higher for the treatments with a pH sensitive coating than Treatments 5 and 6 which do not have a pH sensitive coating. In one example, the ratio for the treatments with a pH sensitive coating is from twofold to tenfold greater than the ratio of a treatment without a pH sensitive coating, in another example fourfold to eightfold greater, and in another example fivefold to sevenfold greater. In one example, the ratio for the treatment with a pH sensitive coating is six fold greater than the ratio of a treatment without a pH sensitive coating. The mean concentration of phenylephrine of Treatment 4 is the closest to Treatment 6 as compared to Treatments 1, 2, and 3. Thus, Treatment 4 was used as a starting point to develop additional prototypes. However, the phenylephrine was released prematurely from Treatment 4 and is thus not ideal. Thus, new prototypes were designed with thicker pH sensitive coatings, to further delay the lag time. It was estimated that it would be most desirable to further delay the lag time by an additional 90-120 minutes.

Example 2

Treatments A-F were made and tested in a randomized, open-label, 7-treatment, 4-period, incomplete crossover in vivo study was performed with 29 healthy adult subjects (male or female, aged 18 to 45 years). Subjects were dosed with study product (investigational treatment A through F and for reference Treatment G, see Table 3 below) and remained on-site for 24 hours post-dosing. Food and activities were standardized for the duration that subjects were at the study site. There was a minimum of a 5-day washout period between treatments with pharmacokinetic blood sampling up to 24 hours post-dose for each treatment.

During confinement, subjects provided blood samples for PK analysis of unconjugated phenylephrine levels at various time points, including before dosing and up to 12 hours after dosing. Safety was assessed through adverse events (AEs), physical examinations, laboratory evaluations and vital signs.

Each of the six multi-particulate composite prototype phenylephrine formulations (Treatments A through F) was an oral capsule comprised of an immediate-release phenylephrine-coated particles component combined with a delayed-release phenylephrine-coated particles component. Treatments A-F are further described in Table 11 and Table 12, hereafter. The six formulations differed in that the delayed-release particles components contained differing doses of phenylephrine HCl (3, 5, or 7 mg) and differing amounts of enteric coating used on particles (expressed as relative weight gain compared to uncoated particles; being 40, 50, or 60% w/w).

Reference Treatment G was 2 Equate™ Suphedrine (immediate-release phenylephrine HCl 10 mg) doses administered 4 hours apart. Equate™ Suphedrine PE, was supplied to the test site as commercially available tablets (Lot #s 3LE1708 and 3LE1845, manufactured by Perrigo® Company [Allegan, Mich.]) with protocol specific labeling.

A summary of the investigational treatments is in Table 3 below.

TABLE 3

Investigational Treatments for Example 2

| Example 2 Treatment | IR Particles Dose PE (mg) | DR Particles Enteric Coating Level (wt %) | Dose PE (mg) | Total dose PE (mg) |
|---|---|---|---|---|
| A | 10 | 40 | 5 | 15 |
| B | 10 | 40 | 7 | 17 |
| C | 10 | 50 | 3 | 13 |
| D | 10 | 50 | 5 | 15 |
| E | 10 | 50 | 7 | 17 |
| F | 10 | 60 | 5 | 15 |

Evaluations included overall $C_{max}$, $AUC_{0-8}$, $AUC_{0-last}$, $AUC_{0-inf}$, partial areas $AUC_{(0-4)}$ and $AUC_{(4-8)}$, $C_{max1}$, $C_{max2}$, $C_{4hr}$, and $C_{8hr}$. Statistical comparisons for each of the extended-release treatments relative to the reference Treatment G for unconjugated phenylephrine are summarized in Table 4, below.

TABLE 4

Pharmacokinetic Parameters and Statistical Comparisons for Unconjugated Phenylephrine

| Comparison[a] | PK Parameter | Test (T)[b] | Reference (R)[b] | T/R Ratio of Means (%) | 90% CI[c] |
|---|---|---|---|---|---|
| Treatment A vs G | $C_{max}$ (pg/mL) | 854.7 | 728.4 | 117.3 | (93.4, 147.4) |
| 15 mg ER | $C_{max1}$ (pg/mL) | 638.2 | 648.6 | 98.4 | (87.5, 110.7) |
| (10 mg IR 5 mg | $C_{max2}$ (pg/mL) | 632.7 | 595.8 | 106.2 | (71.0, 158.8) |
| DR 40% EC) | $C_{4\,hr}$ (pg/mL) | 87.7 | 20.9 | 419.5 | (224.8, 782.7) |
| vs Reference | $C_{8\,hr}$ (pg/mL) | 44.5 | 36.0 | 123.6 | (93.3, 163.7) |
| | $AUC_{0-8}$ (pg · hr/mL) | 1414.6 | 1417.5 | 99.8 | (86.9, 114.7) |
| | $AUC_{0-4}$ (pg · hr/mL) | 802.3 | 688.1 | 116.6 | (102, 133.2) |
| | $AUC_{4-8}$ (pg · hr/mL) | 537.2 | 702.9 | 76.4 | (56.6, 103.1) |
| | $AUC_{0-last}$ (pg · hr/mL) | 1553.3 | 1513.1 | 102.7 | (90.8, 116.1) |
| | $AUC_{0-inf}$ (pg · hr/mL) | 1697.8 | 1593.6 | 106.5 | (94.7, 119.9) |
| Treatment B vs G | $C_{max}$ (pg/mL) | 858.8 | 728.4 | 117.9 | (93.9, 148.0) |
| 17 mg ER | $C_{max1}$ (pg/mL) | 682.2 | 648.6 | 105.2 | (93.5, 118.3) |
| (10 mg IR 7 mg | $C_{max2}$ (pg/mL) | 565.5 | 595.8 | 94.9 | (67.1, 134.3) |
| DR 40% EC) | $C_{4\,hr}$ (pg/mL) | 110.3 | 20.9 | 527.8 | (283.9, 782.7) |
| vs Reference | $C_{8\,hr}$ (pg/mL) | 49.8 | 36.0 | 138.2 | (104.4, 182.9) |
| | $AUC_{0-8}$ (pg · hr/mL) | 1465.7 | 1417.5 | 126.5 | (110.7, 144.5) |
| | $AUC_{0-4}$ (pg · hr/mL) | 870.1 | 688.1 | 116.6 | (102.0, 133.2) |
| | $AUC_{4-8}$ (pg · hr/mL) | 510.6 | 702.9 | 72.6 | (56.9, 92.7) |
| | $AUC_{0-last}$ (pg · hr/mL) | 1642.2 | 1513.1 | 108.5 | (96.0, 122.7) |
| | $AUC_{0-inf}$ (pg · hr/mL) | 1866.0 | 1593.6 | 117.1 | (104.1, 131.8) |
| Treatment C vs G | $C_{max}$ (pg/mL) | 660.4 | 728.4 | 90.7 | (72.2, 113.8) |
| 13 mg ER | $C_{max1}$ (pg/mL) | 616.7 | 648.6 | 95.1 | (84.5, 107.0) |
| (10 mg IR 3 mg | $C_{max2}$ (pg/mL) | 173.9 | 595.8 | 29.2 | (18.4, 46.2) |
| DR 50% EC) | $C_{4\,hr}$ (pg/mL) | 49.0 | 20.9 | 234.5 | (126.1, 435.8) |
| vs Reference | $C_{8\,hr}$ (pg/mL) | 23.5 | 36.0 | 65.3 | (49.4, 86.5) |
| | $AUC_{0-8}$ (pg · hr/mL) | 948.9 | 1417.5 | 66.9 | (58.3, 76.9) |
| | $AUC_{0-4}$ (pg · hr/mL) | 691.1 | 688.1 | 100.4 | (87.9, 114.7) |
| | $AUC_{4-8}$ (pg · hr/mL) | 212.4 | 702.9 | 30.2 | (23.8, 38.3) |
| | $AUC_{0-last}$ (pg · hr/mL) | 1029.4 | 1513.1 | 68.0 | (60.2, 76.9) |
| | $AUC_{0-inf}$ (pg · hr/mL) | 1171.0 | 1593.6 | 73.5 | (65.4, 82.5) |
| Treatment D vs G | $C_{max}$ (pg/mL) | 730.9 | 728.4 | 100.3 | (80.0, 125.9) |
| 15 mg ER | $C_{max1}$ (pg/mL) | 618.9 | 648.6 | 95.4 | (84.8, 107.3) |
| (10 mg IR 5 mg | $C_{max2}$ (pg/mL) | 577.8 | 595.8 | 97.0 | (70.9, 132.7) |
| DR 50% EC) | $C_{4\,hr}$ (pg/mL) | 110.0 | 20.9 | 526.3 | (283.2, 978.2) |
| vs Reference | $C_{8\,hr}$ (pg/mL) | 50.1 | 36.0 | 139.0 | (105.0, 184.0) |
| | $AUC_{0-8}$ (pg · hr/mL) | 1328.6 | 1417.5 | 93.7 | (81.6, 107.6) |
| | $AUC_{0-4}$ (pg · hr/mL) | 835.6 | 688.1 | 121.4 | (106.3, 138.7) |
| | $AUC_{4-8}$ (pg · hr/mL) | 464.9 | 702.9 | 66.1 | (52.3, 83.7) |
| | $AUC_{0-last}$ (pg · hr/mL) | 1487.2 | 1513.1 | 98.3 | (87.0, 111) |
| | $AUC_{0-inf}$ (pg · hr/mL) | 1670.7 | 1593.6 | 104.8 | (93.4, 117.7) |
| Treatment E vs G | $C_{max}$ (pg/mL) | 803.2 | 728.4 | 110.3 | (87.8, 138.5) |
| 17 mg ER | $C_{max1}$ (pg/mL) | 593.9 | 648.6 | 91.6 | (81.4, 103.0) |
| (10 mg IR 7 mg | $C_{max2}$ (pg/mL) | 566.6 | 595.8 | 95.1 | (61.8, 146.4) |
| DR 50% EC) | $C_{4\,hr}$ (pg/mL) | 160.0 | 20.9 | 765.4 | (410.2, 1428.1) |
| vs Reference | $C_{8\,hr}$ (pg/mL) | 61.2 | 36.0 | 169.9 | (128.3, 225.1) |
| | $AUC_{0-8}$ (pg · hr/mL) | 1499.8 | 1417.5 | 105.8 | (92.1, 121.6) |
| | $AUC_{0-4}$ (pg · hr/mL) | 856.2 | 688.1 | 124.4 | (108.9, 142.2) |
| | $AUC_{4-8}$ (pg · hr/mL) | 573.4 | 702.9 | 81.6 | (61.6, 108.0) |
| | $AUC_{0-last}$ (pg · hr/mL) | 1706.3 | 1513.1 | 112.8 | (99.7, 127.5) |
| | $AUC_{0-inf}$ (pg · hr/mL) | 1962.7 | 1593.6 | 123.2 | (109.7, 138.3) |
| Treatment F vs G | $C_{max}$ (pg/mL) | 759.6 | 728.4 | 104.3 | (83.0, 131.0) |
| 15 mg ER | $C_{max1}$ (pg/mL) | 657.4 | 648.6 | 101.4 | (90.1, 114.0) |
| (10 mg IR 5 mg | $C_{max2}$ (pg/mL) | 364.8 | 595.8 | 61.2 | (41.7, 89.9) |
| DR 60% EC) | $C_{4\,hr}$ (pg/mL) | 69.2 | 20.9 | 331.1 | (177.4, 617.7) |
| vs Reference | $C_{8\,hr}$ (pg/mL) | 43.7 | 36.0 | 121.2 | (91.5, 160.6) |
| | $AUC_{0-8}$ (pg · hr/mL) | 1191.1 | 1417.5 | 84.0 | (73.1, 96.5) |
| | $AUC_{0-4}$ (pg · hr/mL) | 790.9 | 688.1 | 114.9 | (100.6, 131.3) |
| | $AUC_{4-8}$ (pg · hr/mL) | 360.4 | 702.9 | 51.3 | (43.8, 60.0) |
| | $AUC_{0-last}$ (pg · hr/mL) | 1335.4 | 1513.1 | 88.3 | (78.1, 99.8) |
| | $AUC_{0-inf}$ (pg · hr/mL) | 1483.1 | 1593.6 | 93.1 | (82.7, 104.7) |

[a]IR: immediate release; DR: delayed release; EC: enteric coating
[b]Values displayed are Least Squares Geometric Mean for all treatments (Test) relative to reference Treatment G (i.e., 10 mg phenylephrine HCl administered q4h for 2 sequential doses)
[c]90% confidence interval (CI) for ratio of test to reference means (expressed as %)

The Example 2 study results demonstrated that Treatment D exhibited a ratio of means and 90% CIs for overall $AUC_{0-8}$, $AUC_{0-last}$, and $AUC_{0-inf}$ that were contained within the 80% to 125% equivalence range relative to the reference Treatment G. The upper bound of the 90% confidence interval for $C_{max}$ from Treatment D was found to be marginally higher than the 125% upper bound relative to the immediate-release treatment. However, the $AUC_{4-8}$ and $C_{max2}$ did not exhibit a ratio of means and 90% CIs within the 80% to 125% equivalence range and therefore Example D may not be bioequivalent, in particular with respect to $AUC_{4-8}$ and $C_{max2}$.

From statistical comparisons of other treatments relative to the reference Treatment G, it was determined that while Treatments B and E exhibited point estimates (ratio of means) that were within the 80-125% equivalence range for several parameters, but they also displayed upper bounds of the 90% confidence interval that were higher than 125% for their respective $C_{max}$ and $AUC_{0-inf}$ values. Additionally, the $AUC_{4-8,\ and}\ C_{max2}$ for Examples B and E did not exhibit a ratio of means and 90% CIs within the 80% to 125% bioequivalence range and therefore Examples B and E may not be bioequivalent, in particular with respect to $AUC_{4-8}$ and $C_{max2}$.

The Example 2 study results demonstrate that the $AUC_{4-8}$, and $C_{max2}$ did not exhibit a ratio of means and 90% CIs within the 80% to 125% equivalence range for Treatments C and F and therefore Examples C and F may not be bioequivalent, in particular with respect to $AUC_{4-8}$, and $C_{max2}$.

The Example 2 study results also demonstrate that the $C_{max}$ did not exhibit a ratio of means and 90% CIs within the 80% to 125% equivalence range for Treatment A and therefore Example A may not be bioequivalent, in particular with respect to $C_{max}$.

Based on the results from Example 2, additional examples were made and tested with higher levels of PE in the ER portion in order to increase the exposure in the 4 to 8 hour interval, including the $AUC_{4-8}$ and $C_{max2}$, so the dosage form meets or exceeds the PK profile of two sequentially administered (every 4 hours) doses of a commercially available immediate release phenylephrine hydrochloride 10 mg reference product.

Example 3

Treatments A-E were made and tested to determine whether higher dose extended-release phenylephrine hydrochloride treatments (total dosages ≥20 mg) could provide systemic exposures to unconjugated phenylephrine that met or exceeded the exposures from two sequentially administered (every 4 hours) doses of a commercially available immediate release phenylephrine hydrochloride 10 mg reference product (Treatment F). Treatments A-E are summarized in Table 5, below. Treatments A-E are further described in Table 13 and Table 14, hereafter.

This study was conducted as a randomized, open-label, 6-treatment, 4-period, incomplete crossover design single-dose study in a total of 30 healthy subjects, with a washout of at least 7 days between dosing for each treatment. The five treatments investigated (Treatments A-E) provided a total single dose of 20 to 40 mg phenylephrine hydrochloride (see Table 5).

Reference Treatment F was 2 Equate™ Suphedrine (immediate-release phenylephrine HCl 10 mg) doses administered 4 hours apart. Equate™ Suphedrine PE, was supplied to the test site as commercially available tablets (Lot# 5LE1574, manufactured by Perrigo® Company [Allegan, Mich.]) with protocol specific labeling.

During confinement, subjects provided blood samples for PK analysis of unconjugated phenylephrine levels at various time points, including before dosing and up to 12 hours after dosing. Bioanalysis of unconjugated phenylephrine in plasma was conducted using a LC/MS-MS method with a LLOQ of 10 pg/mL.

TABLE 5

Investigational Treatments for Example 3

| Example 3 Treatment | IR Particles Dose PE (mg) | DR Particles Enteric Coating Level (wt %) | DR Particles Dose PE (mg) | Total dose PE (mg) |
|---|---|---|---|---|
| A | 10 | 45 | 10 | 20 |
| B | 10 | 45 | 15 | 25 |
| C | 10 | 45 | 20 | 30 |
| D | 15 | 45 | 15 | 30 |
| E* | 20 | 45 | 20 | 40 |

*Example 3, Treatment E is two PE HCl extended-release capsules for a total 40 mg dose (i.e. two capsules of Example A). Treatments A-D are one capsule containing IR and DR portions.

Several pharmacokinetic parameters were evaluated to characterize systemic exposures of unconjugated phenylephrine from the extended-release treatments relative to the immediate-release reference treatment over an 8-hour exposure interval. Results, summarized in Table 6, indicate that the bioavailability for unconjugated phenylephrine was significantly higher for all pharmacokinetic parameters relative to the immediate-release reference treatment. Point estimates for percent ratio of means was ≥100%, and the lower bound of the 90% confidence interval greater than 80%, for most parameters for all five experimental treatments relative to the reference treatment.

TABLE 6

Pharmacokinetic Parameters and Statistical Comparisons for Unconjugated Phenylephrine

| Comparison[a] | PK Parameter | Test (T)[b] | Reference (R)[b] | T/R Ratio of Means (%) | 90% CI[c] |
|---|---|---|---|---|---|
| Treatment A vs F | $C_{max}$ (pg/mL) | 1403.8 | 690.0 | 203.4 | (146.2, 283.1) |
| 20 mg ER | $C_{max1}$ (pg/mL) | 598.0 | 668.7 | 89.4 | (78.6, 101.8) |
| (10 IR + 10 DR) | $C_{max2}$ (pg/mL) | 1028.2 | 587.5 | 175.0 | (105.8, 289.6) |
| vs Reference | $C_{4\ hr}$ (pg/mL) | 168.9 | 12.1 | 1400.7 | (662.9, 2959.6) |
|  | $C_{8\ hr}$ (pg/mL) | 44.8 | 30.6 | 146.7 | (110.3, 195.2) |
|  | $AUC_{0-4}$ (pg · hr/mL) | 949.7 | 597.8 | 158.9 | (124.3, 203.0) |
|  | $AUC_{4-8}$ (pg · hr/mL) | 747.7 | 610.1 | 122.5 | (88.7, 169.4) |
|  | $AUC_{0-last}$ (pg · hr/mL) | 2444.0 | 1370.4 | 178.3 | (154.3, 206.1) |
|  | $AUC_{0-inf}$ (pg · hr/mL) | 2566.6 | 1433.2 | 179.1 | (156.3, 205.2) |
| Treatment B vs F | $C_{max}$ (pg/mL) | 1938.3 | 690.0 | 280.9 | (201.9, 390.9) |
| 25 mg ER | $C_{max1}$ (pg/mL) | 689.3 | 668.7 | 103.1 | (90.6, 117.3) |
| (10 IR + 15 DR) | $C_{max2}$ (pg/mL) | 1557.1 | 587.5 | 265.0 | (160.2, 438.5) |
| vs Reference | $C_{4\ hr}$ (pg/mL) | 187.2 | 12.1 | 1552.5 | (734.7, 3280.5) |
|  | $C_{8\ hr}$ (pg/mL) | 80.1 | 30.6 | 262.1 | (197.0, 348.7) |
|  | $AUC_{0-4}$ (pg · hr/mL) | 1046.8 | 597.8 | 175.1 | (137.0, 223.8) |
|  | $AUC_{4-8}$ (pg · hr/mL) | 1151.6 | 610.1 | 188.7 | (125.8, 283.2) |

TABLE 6-continued

Pharmacokinetic Parameters and Statistical Comparisons for Unconjugated Phenylephrine

| Comparison[a] | PK Parameter | Test (T)[b] | Reference (R)[b] | T/R Ratio of Means (%) | 90% CI[c] |
|---|---|---|---|---|---|
| | $AUC_{0\text{-}last}$ (pg · hr/mL) | 3339.2 | 1370.4 | 243.7 | (210.8, 281.6) |
| | $AUC_{0\text{-}inf}$ (pg · hr/mL) | 3535.1 | 1433.2 | 246.7 | (215.2, 282.7) |
| Treatment C vs F | $C_{max}$ (pg/mL) | 3533.7 | 690.0 | 512.1 | (368.0, 712.6) |
| 30 mg ER | $C_{max1}$ (pg/mL) | 620.2 | 668.7 | 92.7 | (81.5, 105.6) |
| (10 IR + 20 DR) | $C_{max2}$ (pg/mL) | 3027.2 | 587.5 | 515.3 | (311.4, 852.5) |
| vs Reference | $C_{4\ hr}$ (pg/mL) | 213.8 | 12.1 | 1772.5 | (838.8, 3745.2) |
| | $C_{8\ hr}$ (pg/mL) | 122.4 | 30.6 | 400.6 | (301.1, 523.9) |
| | $AUC_{0\text{-}4}$ (pg · hr/mL) | 1211.7 | 597.8 | 202.7 | (158.6, 259.1) |
| | $AUC_{4\text{-}8}$ (pg · hr/mL) | 2155.7 | 610.1 | 353.3 | (227.5, 548.7) |
| | $AUC_{0\text{-}last}$ (pg · hr/mL) | 5551.2 | 1370.4 | 405.1 | (350.5, 468.2) |
| | $AUC_{0\text{-}inf}$ (pg · hr/mL) | 5823.5 | 1433.2 | 406.3 | (354.6, 465.6) |
| Treatment D vs F | Cmax (pg/mL) | 2342.8 | 690.0 | 339.5 | (243.7, 473.0) |
| 30 mg ER | $C_{max1}$ (pg/mL) | 1090.7 | 668.7 | 163.1 | (143.2, 185.7) |
| (15 IR + 15 DR) | $C_{max2}$ (pg/mL) | 1683.1 | 587.5 | 286.5 | (172.8, 474.9) |
| vs Reference | $C_{4\ hr}$ (pg/mL) | 259.8 | 12.1 | 2154.5 | (1016.8, 4565.1) |
| | $C_{8\ hr}$ (pg/mL) | 71.9 | 30.6 | 235.3 | (176.7, 313.4) |
| | $AUC_{0\text{-}4}$ (pg · hr/mL) | 1658.1 | 597.8 | 277.4 | (216.8, 354.8) |
| | $AUC_{4\text{-}8}$ (pg · hr/mL) | 1316.4 | 610.1 | 215.8 | (147.4, 315.7) |
| | $AUC_{0\text{-}last}$ (pg · hr/mL) | 4230.5 | 1370.4 | 308.7 | (266.9, 357.0) |
| | $AUC_{0\text{-}inf}$ (pg · hr/mL) | 4388.3 | 1433.2 | 306.2 | (267.1, 351.1) |
| Treatment E vs F | Cmax (pg/mL) | 2487.1 | 690.0 | 360.4 | (259.0, 501.5) |
| 40 mg ER | $C_{max1}$ (pg/mL) | 1413.8 | 668.7 | 211.4 | (185.8, 240.6) |
| (20 IR + 20 DR)[d] | $C_{max2}$ (pg/mL) | 1995.6 | 587.5 | 339.7 | (205.3, 562.0) |
| vs Reference | $C_{4\ hr}$ (pg/mL) | 365.7 | 12.1 | 3032.7 | (1435.3, 6408.1) |
| | $C_{8\ hr}$ (pg/mL) | 135.3 | 30.6 | 442.7 | (332.7, 588.9) |
| | $AUC_{0\text{-}4}$ (pg · hr/mL) | 2142.0 | 597.8 | 358.3 | (280.3, 457.9) |
| | $AUC_{4\text{-}8}$ (pg · hr/mL) | 1761.9 | 610.1 | 288.8 | (217.2, 383.9) |
| | $AUC_{0\text{-}last}$ (pg · hr/mL) | 5667.7 | 1370.4 | 413.6 | (357.8, 478.0) |
| | $AUC_{0\text{-}inf}$ (pg · hr/mL) | 5959.1 | 1433.2 | 415.8 | (362.8, 476.5) |

Figure 5A:
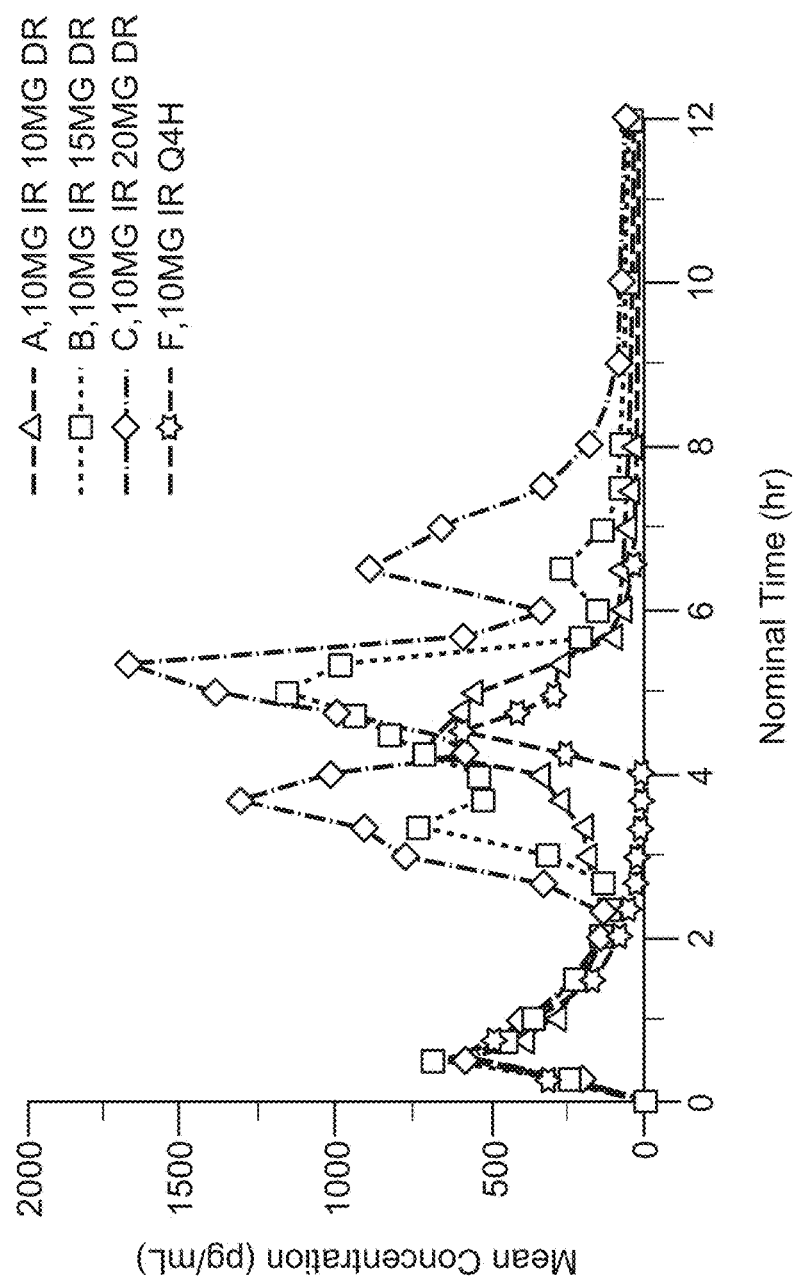
FIG. 5A shows the mean unconjugated phenylephrine concentration for Example 3, Treatments A, B, and C versus Reference Treatment F.
Figure 5B:
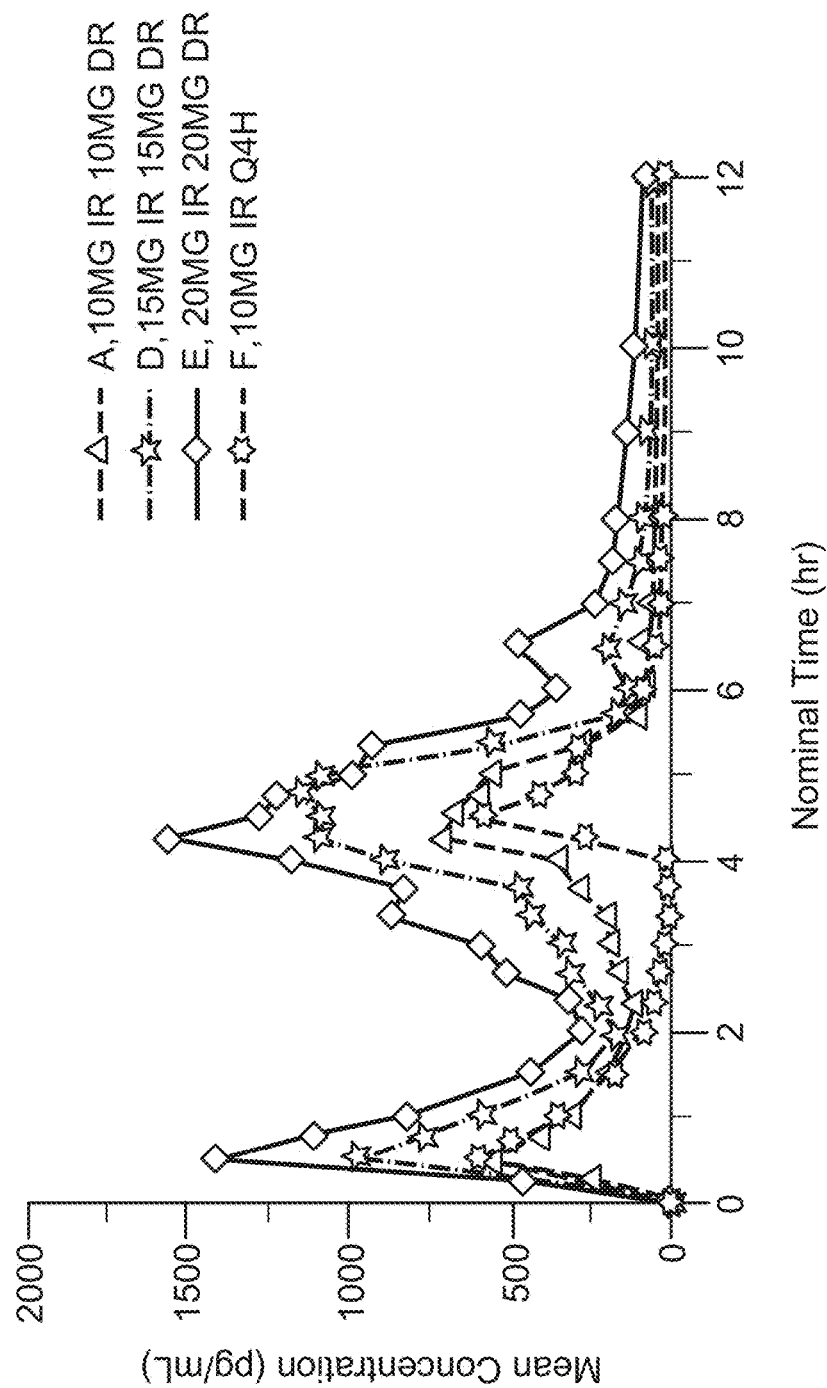
FIG. 5B shows the mean unconjugated phenylephrine concentration for Example 3, Treatments A, D, and E versus Reference Treatment F.
Figure 5C:
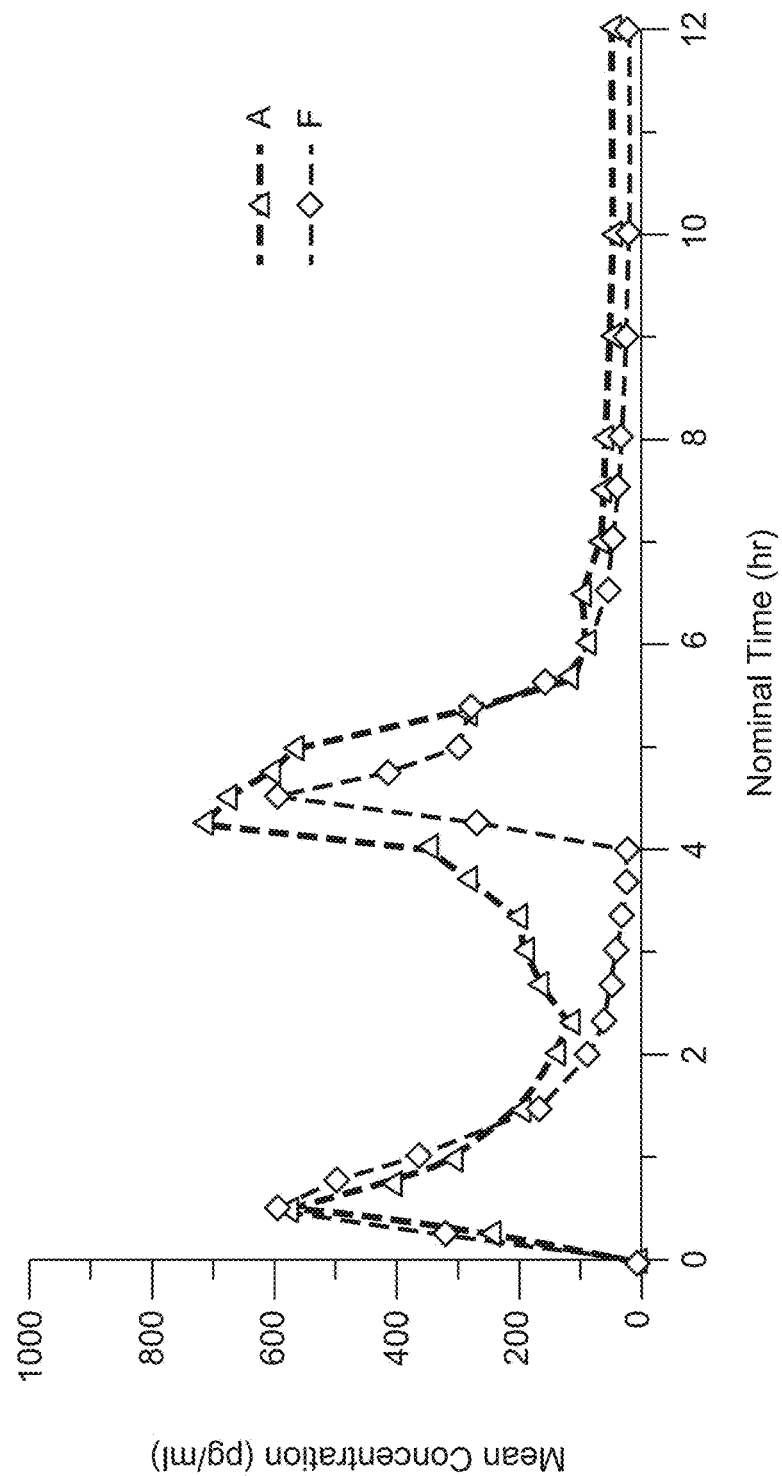
FIG. 5C shows the mean unconjugated phenylephrine concentration for Example 3, Treatment A versus Reference Treatment F.

[a]IR: immediate release; DR: delayed release; EC: enteric coating
[b]Values displayed are Least Squares Geometric Mean for all treatments (Test) relative to reference Treatment G (i.e., 10 mg phenylephrine HCl administered q4h for 2 sequential doses)
[c]90% confidence interval (CI) for ratio of test to reference means (expressed as %)
[d]Treatment E (40 mg ER) was dosed as 2 × 20 mg Treatment A capsules (each capsule containing 10 IR + 10 DR)
Statistical methodology note: $AUC_{4\text{-}8}$ allows residual variance to vary by treatment group. Other parameters use traditional constant variance assumptions FIGS. 5A, B, and C show the mean unconjugated phenylephrine concentration for Treatments A-E versus Reference Treatment F. In particular FIG. 5A shows A, B, and C versus Reference Treatment F, FIG. 5B shows Treatments A, D, and E versus Reference Treatment F, and FIG. 5C shows Treatment A versus Reference Treatment F. The pharmacokinetic results from Example 3 illustrate that Treatments A-E all delivered phenylephrine exposures over the entire dosing interval, as well as over the 0-4 hour and 4-8 hour intervals post dosing, meeting or exceeding the corresponding exposures of the immediate-release reference, as noted from overall AUC(0-tlast), AUC(0-inf), AUC(0-4), and AUC(4-8).

Treatment A (20 mg extended-release phenylephrine hydrochloride) could be a preferred treatment, since it has the lowest dosage extended-release treatment providing an exposure profile that meets or exceeds the exposure profile of the reference product.

Safety variables, including blood pressure (BP), heart rate (pulse, HR), and ECG parameters were assessed for Treatments A-E vs. the control (Treatment F: Equate® Suphedrine PE, 10 mg phenylephrine hydrochloride administered q4h for 2 sequential doses). BP and HR variations potentially associated with the study treatments after dosing were compared to the reference treatment.

Overall, the study treatments all showed a similar safety profile: no significant changes in blood pressure, heart rate, or ECG parameters were associated with any specific treatment. In summary, all investigational treatments were considered safe, and were well tolerated by the subjects participating in the study.

Example 4

The amount of phenylephrine released was calculated using an HPLC Assay, as described below. When the amount of phenylephrine released is greater than the acid limit, which is about 10%, this is the lag time. While not wishing to be bound by theory, it is believed that the Krebs buffer, which contains bicarbonate, is a better approximation for the conditions in the digestive tract than other dissolution methods, which use phosphate buffers, and can lead to better approximations for delayed release particles.

Figure 6:
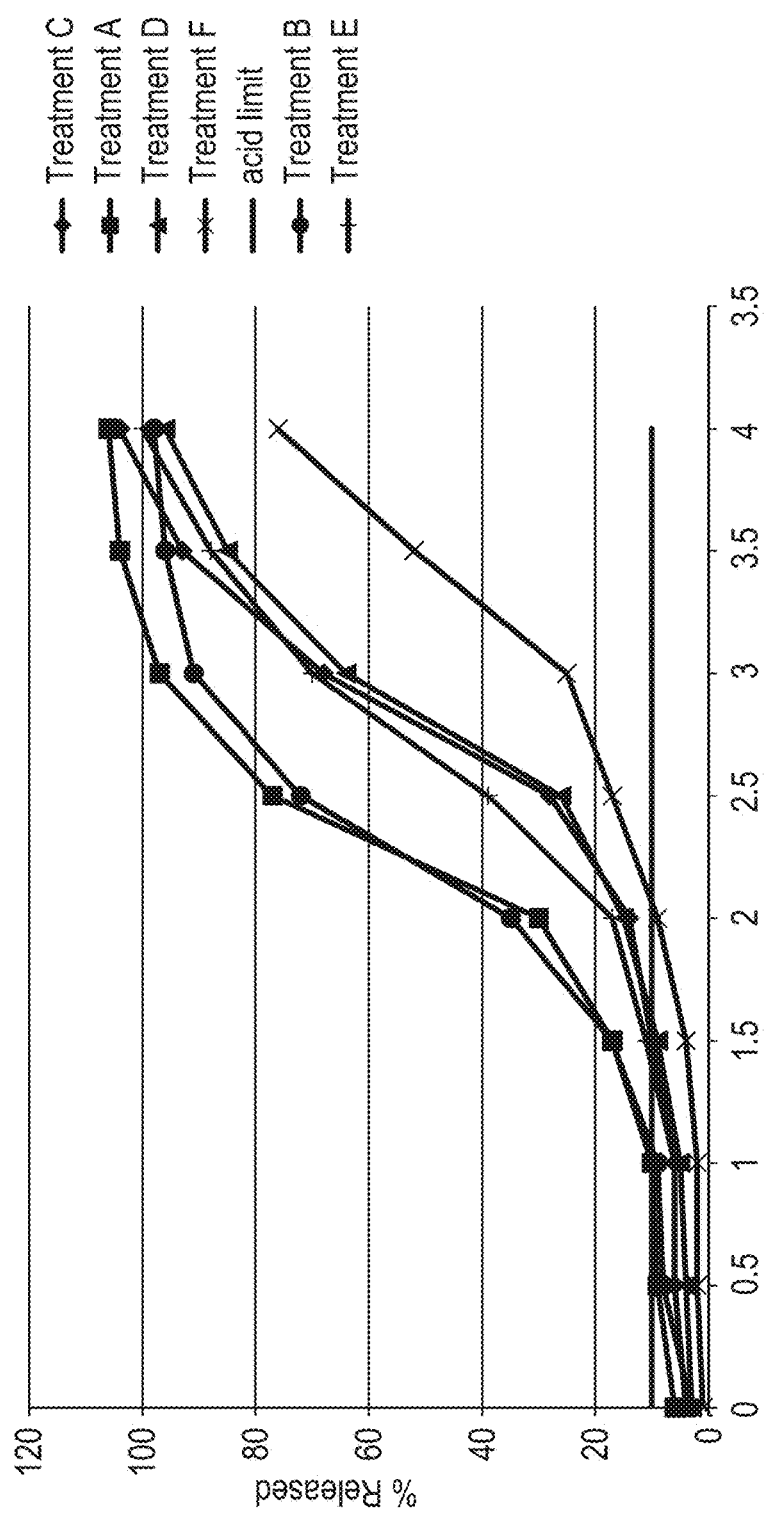
FIG. 6 shows the mean percent dissolved phenylephrine, in vitro using the Krebs Buffer Dissolution Method, over time for different formulation prototypes.

FIG. 6 shows the amount of phenylephrine released, in vitro using the Krebs Buffer Dissolution Method, as described below, over time with different formulation prototypes. The prototypes shown in FIG. 6 and Table 7, below, correspond to Treatments A-F. Treatments A-F are further described in Table 11 and Table 12, hereafter.

TABLE 7

| Delayed release particles | Amount phenylephrine (mg) | % wt gain of pH sensitive coating | Prototype lag time in Krebs Buffer (hours) |
|---|---|---|---|
| Treatment C | 3 | 50 | 2 |
| Treatment A | 5 | 40 | 1.5 |

TABLE 7-continued

| Delayed release particles | Amount phenylephrine (mg) | % wt gain of pH sensitive coating | Prototype lag time in Krebs Buffer (hours) |
|---|---|---|---|
| Treatment D | 5 | 50 | 2 |
| Treatment F | 5 | 60 | 2.4 |
| Treatment B | 7 | 40 | 1.5 |
| Treatment E | 7 | 50 | 2 |

In one example, the lag time as determined by following the Krebs Buffer Method is from about 0.5 hours to about 6 hours, in another example from about 1 hour to about 4 hours, in another example from about 1.25 hours to about 3 hours, and in another example from about 1.5 hours to about 2.5 hours.

In one example, the AUC, including the $AUC_{0-4}$, $AUC_{0-8}$, $AUC_{4-8}$, $AUC_{0-inf}$, and/or $AUC_{0-last}$, for a dosage form that can be administered every eight hours can meet or exceed the AUC for two 10 mg immediate release doses administered every four hours. In another example, the AUC for a dosage form that can be administered every twelve hours can meet or exceed the AUC for three 10 mg immediate release doses administered every four hours. In such a dosage form, $C_{max}$ for the novel form can meet or exceed the immediate release form dosed every 4 hours for a total of two or three doses.

In another example, the AUC for a dosage form that can be administered every eight hours can be substantially equivalent or greater than the AUC for two 10 mg immediate release doses administered every four hours. In another example, the AUC for a dosage form that can be administered every twelve hours can be substantially equivalent or greater than the AUC for three 10 mg immediate release doses administered every four hours. In such a dosage form, $C_{max}$ for the novel form can also be substantially equivalent or greater than the immediate release form dosed every 4 hours for a total of two or three doses.

In another example, the dosage form can have a higher AUC and/or $C_{max}$ for the immediate release particles and the delayed release particles as compared to the AUC and/or $C_{max}$ for 10 mg immediate release doses administered every four hours.

In order to provide delayed release phenylephrine dosage forms, the dosage form can be properly formulated.

The dosage form can contain a plurality of particles. The term particle is not meant to be limiting and can include microcrystals, micro-particles, beads, microbeads, powders, granules, pellets, micropellets, nonpareil seeds, and microcapsules. In one example the particle is from about 200 μm to about 1500 μm in its longest dimension, in another example about 300 μm to about 1000 μm, in another example about 400 μm to about 800 μm, and in another example about 500 μm to about 725 μm. In another example, the particles can be about 700 μm to about 925 μm in its longest diameter. In another example, the particles are spherical or substantially spherical. In another example, the dosage form contains at least 100 delayed release particles, in another example at least 200 delayed release particles, in another example at least 300 delayed release particles, in another example at least 400 delayed release particles, in another example at least 500 delayed release particles, in another example at least 600 delayed release particles, and in another example at least 750 delayed release particles.

Figure 7B:
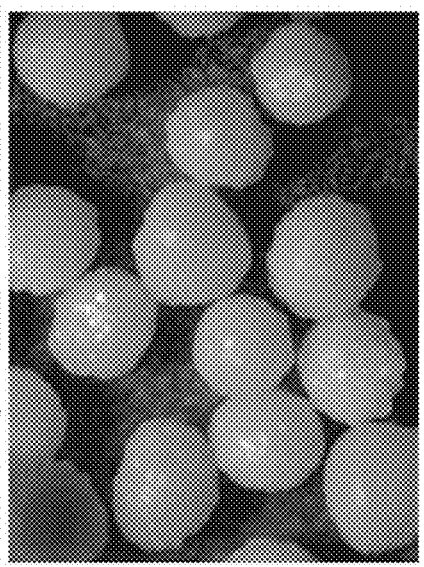
FIGS. 7A, 7B, 7C, and 7D show digital photographs of delayed release particles under a total magnification of 40×.
Figure 7D:
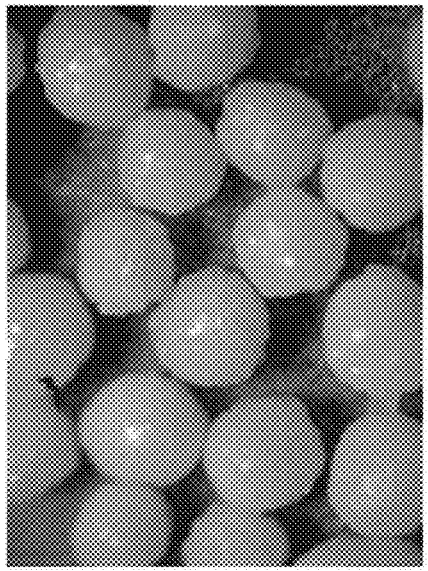
Figure 7A:
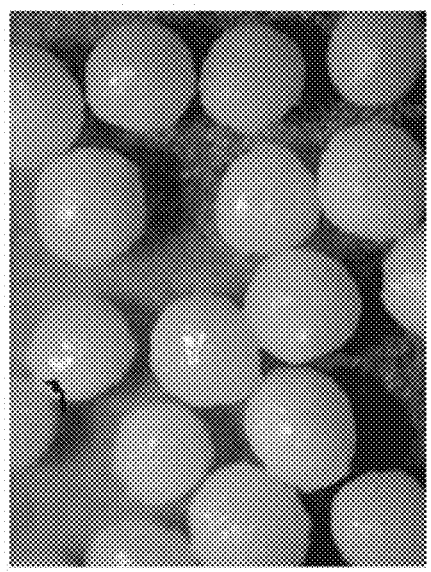
Figure 7C:
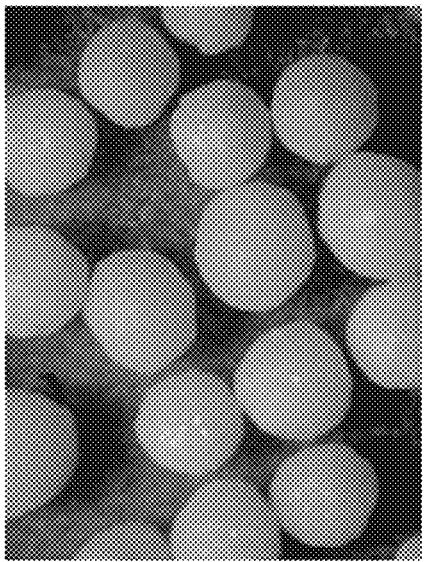
Figure 8A:
FIGS. 8A, 8B, 8C, and 8D show digital photographs of delayed release particles under a total magnification of 40×.
Figure 8B:
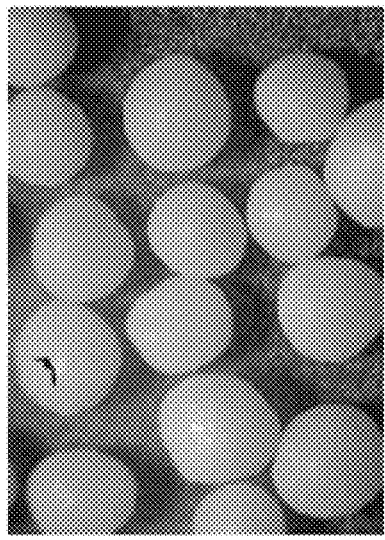
Figure 8C:
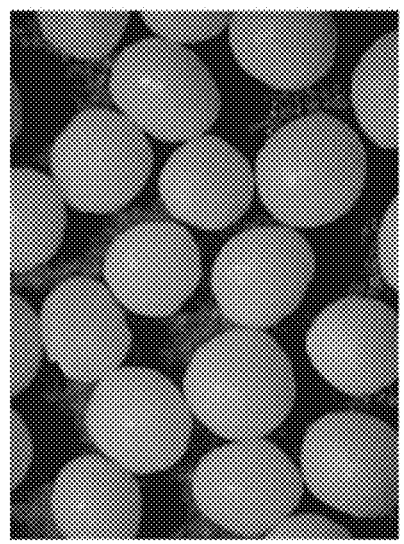
Figure 8D:
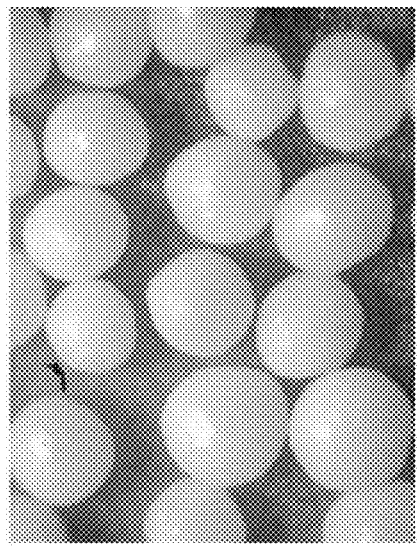

In another example, the delayed release particles can be substantially smooth. If the delayed release particles are not smooth, for instance if they are spiked or have a rough surface appearance, the dissolution can be altered. If the particles are spiked or have a rough surface, the release of phenylephrine can be early as the phenylephrine can leak out of the portions of the particles that have the thinnest coating level. In one example, the particles are substantially smooth, as visually perceived under a microscope with a total magnification of 40×. As used herein, "visually perceived under a microscope" means that a human viewer can visually discern that the particle is smooth and the surface has an appearance that is substantially similar to a particle without a pH sensitive coating under a properly focused microscope with a total magnification of 40×. FIGS. 7A, B, C and D show digital photographs of particles that are not substantially smooth as can be visually perceived under a microscope with a total magnification of 40×. FIGS. 8A, B, C, and D show digital photographs of particles that are substantially smooth as can be visually perceived under a microscope with a total magnification of 40×. The substantially smooth particles can be out-of-round and still smooth.

In another example, smoothness can be determined by the Smoothness Test Method, as described hereafter. In one example, the particles can have a mean circularity from about 0.70 to about 1, in another example from about 0.75 to about 1, in another example from about 0.8 to about 1, in another example from about 0.85 to about 1, in another example from about 0.90 to about 1, and in another example from about 0.95 to about 1. In another example particles can have a mean circularity from about 0.72 to about 0.95, to about 0.78 to about 0.93, and from about 0.82 to about 0.89.

In one example, the dosage form can deliver a therapeutic blood plasma concentration of unconjugated phenylephrine for at least 6 hours, in another example for at least 8 hours, in another example for at least 10 hours, and in another example for at least 12 hours.

The core of the particles in the present dose form can contain any pharmaceutically suitable material. Non-limiting examples of core materials can consist of microcrystalline cellulose, sugars, starches, polymers, and combinations thereof. In one example, the core can be microcrystalline cellulose spheres marketed under the tradename "Cellets®" available from Glatt® Air Techniques Inc., Ramsey, N.J. In one example, the microcrystalline cellulose spheres can have a diameter of about 500 μm to about 710 μm and a bulk density of about 0.7 g/cc to about 0.9 g/cc. In one example, at least about 85% have a diameter of about 500 μm to about 710 μm.

The delayed release particles can contain a pH sensitive coating which means that the coating dissolves when it is immersed in a particular pH, which can be basic or acidic. In one example the pH sensitive coating is an enteric coating. It can be important for the coating to be the appropriate thickness or appropriate weight percentage. If the coating is too thin or the weight percentage is too low, then the phenylephrine can be released too early relative and the lag time can be shorter than required. One problem with releasing the phenylephrine too early is that the doses can be too close together and the user may not have a sustained level of unconjugated phenylephrine for the intended duration.

If the coating is too thick or if the weight percentage is too high, then the phenylephrine can be released suboptimally with respect to achieving the intended 6-12 hour duration of dosing. If the phenylephrine is released too distally in the small intestine then there may not be enough time for the phenylephrine to enter the blood stream before entering the colon. While not wishing to be bound by theory, the colon may not have enough liquid to allow the dissolution of phenylephrine and a reduced surface area to allow for systemic absorption. Therefore it can be advantageous for significant dissolution of the dose form and active to occur prior to migration into the colon.

The weight percent (wt. %) increase of the particle after the pH sensitive coating is added can be from about a 30 wt. % to about a 60 wt. % increase, in another example from about a 35 wt. % to about a 55 wt. %, in another example from about a 37% to about a 53%, in another example from about a 40 wt. % to about a 50 wt. %, and in another example from about a 43% to about a 47%.

In another example, the wt. % increase of the particle after the pH sensitive coating is added can be from about a 35 wt. % to about a 70 wt. % increase, from about a 40 wt. % to about a 65 wt. %, from about a 42 wt. % to about a 60 wt. %, from about a 45 wt. % to about a 57 wt. %, and from about a 48 wt. % to about a 53 wt. %.

In another example, the wt. % increase of the particle after the pH sensitive coating is added can be from about a 15 wt. % to about a 65 wt. % increase, in another example from about a 25 wt. % to about a 55 wt. % increase, and in another example from about a 35 wt. % to about a 45 wt. % increase.

In another example, the wt. % increase after the pH sensitive coating is added can be from about a 25 wt. % to about a 75 wt. % increase, in another example from about a 35 wt. % to about a 45 wt. % increase, and in another example from about a 45 wt. % to about a 55 wt. % increase.

In another example, the wt. % increase after the pH sensitive coating is added can be from about a 40 wt. % to about a 80 wt. % increase, in another example from about a 50 wt. % to about a 75 wt. % increase, and in another example from about a 55 wt. % to about a 65 wt. % increase.

In another example, the wt. % increase after the pH sensitive coating is added is from 20 wt. % to about 60 wt. %, in another example from about 30 wt. % to about 55 wt. %, in another example from about 40 wt. % to about 50 wt. %, in another example from about 42 wt. % to about 48 wt. %, in another example from about 44 wt. % to about 46 wt. %, and in another example about 45 wt. %. The wt. % increase after the pH sensitive coating is added is from about 10 wt. % to about 50 wt. %, in another example from about 20 wt. % to about 45 wt. %, in another example from about 30 wt. % to about 40 wt. %, in another example from about 32 wt. % to about 38 wt. %, in another example from about 34 wt. % to about 36 wt. %, and in another example about 35 wt. %. In another example, the wt. % increase after the pH sensitive coating is added is from about 30 wt. % to about 50 wt. % and in another example from about 35 wt. % to about 45 wt. %.

In another example, the delayed release particles can optionally comprise from about a 5 wt. % to about a 55 wt. % pH sensitive coating, by weight of the particle, in another example from about a 10 wt. % to about a 45 wt. %, and in another example from about a 15 wt. % to about a 35 wt. %.

In another example, the pH sensitive coating is from about 10 μm to about 200 μm thick, in another example from about 15 μm to about 150 μm, in another example from about 25 μm to about 125 μm, in another example from about 30 μm to about 100 μm, in another example from about 40 μm to about 80 μm, in another example from about 45 μm to about 75 μm, in another example from about 50 μm to about 70 μm, in another example from about 55 μm to about 65 μm, and in another example from about 57 μm to about 63 μm. In one example, the pH sensitive coating can be about 60 μm thick.

In another example, the delayed release particle contains one or more coatings and the total thickness of the coatings is from about 20 μm to about 300 μm thick, in another example from about 40 μm to about 200 μm, in another example from about 60 μm to about 175 μm, in another example from about 70 μm to about 150 μm, in another example from about 75 μm to about 125 μm, in another example from about 85 μm to about 115 μm, and in another example from about 90 μm to about 110 μm. In one example the one or more coatings can be about 100 μm thick.

The pH sensitive coating can be an enteric coating. In one example, the pH sensitive coating can be degradable in the small intestine at a pH of at least 5.5 and in another example the pH coating can be degradable when the pH is at least 7.0. In another example, the pH sensitive coating can be degradable at a pH from about 5-9, in another example about 6-8, and in another example from about 6.5-7.5. In any event, in one example, the pH sensitive coating can avoid degradation premature phenylephrine dissolution in the low pH in the stomach.

The pH sensitive coating can contain one or more polymers alone or in combination with water soluble or insoluble polymers. The pH sensitive coating can contain any chemically stable, biocompatible polymer. In one example, the pH sensitive coating has a weight average molecular weight of from 100,000 g/mol to 600,000 g/mol, in another example 150,000 g/mol to 500,000 g/mol, in another example 200,000 g/mol to 400,000 g/mol, in another example 225,000 g/mol to 350,000 g/mol, and in another example 250,000 g/mol to 300,000 g/mol.

Non-limiting examples of polymers can include cellulose esters and derivatives, acrylate copolymers, hypromellose acetate succinate, polyvinyl acetates and derivatives (commercially available as Kollicoat®, from BASF, Tarrytown, N.J.), shellac, and combinations thereof.

Non-limiting examples of cellulose esters and derivatives can include cellulose acetate phthalate, hydroxypropyl methylcellulose phthalate (HPMCP), hydroxypropyl methylcellulose acetate succinate, cellulose acetate tetrahydrophthalate, cellulose acetate hexahydrophthalate, hydroxypropyl cellulose acetate succinate, and combinations thereof.

Non-limiting examples of acrylate copolymers can include methyl-methacrylate esters copolymerized with methacrylic acid, acrylic acid and esters copolymerized with methacrylic acid and esters, ammonio-containing acrylate copolymers, and combinations thereof.

In one example, the polymer can be an anionic copolymer based on methyl acrylate, methyl methacrylate, and methacrylic acid. In one example, the coating can contain Poly (methyl acrylate-co-methyl methacrylate-co-methacrylic acid) 7:3:1 polymer marketed under the tradename "Eudragit® FS30D", available from Evonik Industries, Darmstadt, Germany In another example, the coating can further comprise Poly(methacrylic acid-co-ethyl acrylate) 1:1 polymer, marketed under the tradename "Eudragit® L30D", commercially available from Evonik, Darmstadt, Germany.

In one example, the pH sensitive coating can contain both Eudragit® FS3OD and Eudragit® L30D. In one example, the pH sensitive coating can contain from 50% to 95% FS30D, by weight of the total Eudragit®, in another example 60% to 90%, and in another example 70% to 85%. In one example, the pH sensitive coating can contain 85% FS3OD and 15% L30D by weight of the Eudragit®, in another example the pH sensitive coating can contain 90% FS3OD and 10% L30D, and in another example the pH sensitive coating can contain 100% FS30D.

In one example, the pH sensitive coating can contain more than one polymer that can be mixed at any ratio to control where the phenylephrine is released.

In one example, the immediate release particles can have a polymer coating, which is not an enteric coating and can dissolve upon entering the stomach.

In another example, the % of phenylephrine in the dosage form and/or the immediate release dosage forms and/or the delayed release particles can contain from about 2% to about 20%, in another example from about 5% to about 15%, in another example from about 7% to about 12%, in another example from about 8% to about 10%, and in another example from about 7% to about 9%. In another example, the % of phenylephrine in the dosage form and/or the immediate release dosage forms and/or the delayed release particles can be greater than about 5%, in another example greater than about 6%, in another example greater than about 7%, in another example greater than about 8%, in another example greater than about 9%, in another example greater than about 10%, in another example greater than about 11%, and in another example greater than about 12%. In another example, the % of phenylephrine in the dosage form and/or the immediate release dosage forms and/or the delayed release particles can be less than about 25%, in another example less than about 20%, in another example less than about 15%, in another example less than about 12%, and in another example less than about 10%. In another example, the % of phenylephrine in the dosage form and/or the immediate release dosage forms and/or the delayed release particles can be from about 8% to about 30%, in another example from about 10% to about 25%, in another example from about 12% to about 20%, and in another example from about 13% to about 18%. In another example, the % of phenylephrine in the dosage form and/or the immediate release dosage forms and/or the delayed release particles can be from about 10% to 75%, in another example from 20% to 50%, and in another example from 30% to 40%.

The ratio of immediate release particles or other immediate release forms to delayed release particles can vary. In one example, each immediate release form can contain the same amount of phenylephrine as each delayed release particle and the ratio of immediate release form to delayed release particle can be adjusted to achieve the desired dose and effect. In another example, the ratio of the amount of phenylephrine with the immediate release forms to the amount of phenylephrine coated on the delayed release particles can be greater than about 1:1. In another example, the ratio of the amount of phenylephrine with the immediate release forms to the amount of phenylephrine coated on the delayed release particles can be less than about 1:1. And in another example, the ratio of the amount of phenylephrine with the immediate release forms to the amount of phenylephrine on the delayed release particles can be equal to about 1:1. In one example, the ratio of the amount of phenylephrine with the immediate release forms to the amount of phenylephrine coated on the delayed release particles can be from about 1:4 to about 4:1, in another example from about 1:3 to about 3:1, and in another example from about 1:2 to about 2:1. In another example, the ratio of the amount of phenylephrine with the immediate release forms to the amount of phenylephrine on the delayed release particles can be from 1:1 to 1:5, in another example from 1:1.5 to 1:4, in another example from 1:2 to 1:3, and in another example from 1:2.5 to 1:2.75. In another example, the ratio of the amount of phenylephrine with the immediate release forms to the amount of phenylephrine coated on delayed release particles can be greater than about 1:5, in another example greater than about 1:4, in another example greater than about 1:3, in another example greater than about 1:2 and in another example greater than about 1:1. If the ratio is not optimal, then the product may not achieve the desired dosing regimen, e.g. once every 6-12 hours.

In another example, the amount of phenylephrine on each immediate release particle or other immediate release forms can be different than the amount of phenylephrine on each delayed release particle. In another example, the immediate release particles or other immediate release form can contain more phenylephrine than the delayed release particles and the amount of phenylephrine is adjusted via the amount coated onto each particle. In another example, the immediate release particles or other immediate release forms can contain less phenylephrine than the delayed release particles and the amount of phenylephrine is adjusted via the amount coated onto each particle. In another example, the immediate release particles or other immediate release form can contain approximately the same amount of phenylephrine as the delayed release particles.

The ratio of immediate release particles or other immediate release form to delayed release particles can be adjusted depending on the desired PK profile. In one example, the PK profile can be substantially equivalent to an immediate release dose form administered every four hours. In another example, the PK profile is greater than the PK profile of multiple immediate release dose forms administered every four hours and is considered safe and effective for an OTC decongestion product. In another example, the PK profile is not substantially equivalent to a the PK profile of multiple immediate release dose forms administered every four hours but is considered to be safe and effective for an OTC decongestion product.

In one example, the multi-particle dosage form can have two pulses, can be administered every eight hours, and can be substantially equivalent to the PK profile for two four hour doses of a commercially available phenylephrine product. In another example, the multi-particle dosage form can have two pulses, can be administered every eight hours, and can have a minimum PK profile that is substantially bioequivalent to the PK profile for two four hour doses of a commercially available phenylephrine product. In another example, the multi-particle dose form can contain both immediate and delayed release phenylephrine particles and can be administered every 6-8 hours and can have a PK profile that substantially surpasses the PK profile phenylephrine from commercially available phenylephrine product dosed every 4 hours. In one example the immediate release particles or other immediate release form and the delayed release particles can have the same amount of phenylephrine, the weight ratio of immediate release particles to delayed release particles can be from about 1:1 to about 10:1, in another example the weight ratio can range from about 1:1 to about 4:1.

In one example, a dose can contains both IR and DR forms and the dose can contain from about 5 mg to about 100 mg phenylephrine hydrochloride, in another example from about 10 mg to about 75 mg, in another example from about 15 mg to about 60 mg, and in another example from about 20 mg to about 50 mg. In another example, a dose can contain from about 5 mg to about 40 mg phenylephrine hydrochloride, in another example from about 7 mg to about 30 mg, in another example from about 10 mg to about 25 mg, and in another example from about 10 mg to about 20 mg. In one example, a dose can contain 20 mg phenylephrine hydrochloride.

In one example, the dosage form can contain at least an immediate release form, for instance, immediate release particles, powders, granules, beads. In one example, the immediate release form can be a liquid. In another example the immediate release form can be a solid. In another example the dosage form can contain a plurality of immediate release forms and in another example the dosage form can contain a couple of immediate release dosage forms and in another example the dosage form can contain a single immediate release dosage form. In each dose, the immediate release form can contain from about 3 mg to about 20 mg phenylephrine hydrochloride, in another example from about 5 mg to about 15 mg, in another example from about 7 mg to about 12 mg, and in another example from about 9 mg to about 11 mg. In one example, a dose can contain 10 mg phenylephrine hydrochloride in the immediate release form.

The dosage form can contain at least a delayed release form, in particular, delayed release particles. The delayed release particles can have a coating that contains phenylephrine hydrochloride and the coating can substantially surround a core. In one example, the core is substantially free or free of phenylephrine. In another example, the core is not seeded with phenylephrine, where seeded means that the phenylephrine is dispersed throughout the core.

In another example, the dosage form can contain at least a delayed release form and each dose can contain phenylephrine hydrochloride, in one example the dose can contain from about 5 mg to about 40 mg PE in the delayed release form, in another example from about 7 mg to about 35 mg, and in another example from about 10 mg to about 30 mg. In another example, a dose of the delayed release form can contain from about 5 mg to about 20 mg phenylephrine hydrochloride, in another example from about 7 mg to about 15 mg, and in another example about 10 mg. In another example, a dose of the delayed release form can contain from about 10 to about 30 mg phenylephrine hydrochloride, in another example about 15 mg to about 25 mg, and in another example about 20 mg. In another example, a dose of the delayed release form can contain from about 3 mg to about 9 mg phenylephrine, in another example from about 5 mg to about 8 mg, and in another example about 7 mg.

In another example the dosage form can contain a delayed release form that can contain less phenylephrine than the immediate release particles or other immediate release forms. In another example, a dose of the delayed release particles can contain less than about 20 mg of phenylephrine, in another example less than about 15 mg phenylephrine, and in another example less than about 10 mg phenylephrine. In another example a dose of the delayed release form can contain from about 2 mg to about 9 mg phenylephrine, in another example from about 3 mg to about 7 mg phenylephrine, and in another example from about 4 mg to about 6 mg of phenylephrine. In another example, a dose of the delayed release form can contain from about 1 mg to about 5 mg phenylephrine, in another example from about 2 mg to about 4 mg, and in another example about 3 mg. In another example, a dose of the delayed release form can contain from about 2 to about 7 mg phenylephrine, in another example about 3 mg to about 6 mg, and in another example about 5 mg. In another example, a dose of the delayed release form can contain from about 3 mg to about 9 mg phenylephrine, in another example from about 5 mg to about 8 mg, and in another example about 7 mg.

In another example, the parameters including $C_{max}$, $C_{max1}$, $C_{max2}$, $C_{4hr}$, $C_{8hr}$, $AUC_{0-4}$, $AUC_{4-8}$, $AUC_{0-last}$, and/or $AUC_{0-inf}$, for the pulsatile dosage form can meet or exceed systemic exposures relative to a commercially available, immediate release PE dose taken at 4 hour intervals while remaining safe and effective. In one example, the ratio of means for pulsatile PE dosage form relative to the IR treatment of one or more parameters can be at least about 85%, at least about 90%, at least about 95%, at least about 100%, at least about 110%, at least about 120%, at least about 130%, at least about 135%, at least about 140%, at least about 145%, at least about 150%, at least about 155%, at least about 165%, at least about 170%, at least about 175%, and at least 200%. In one example, the lower bound of the 90% confidence interval of one or more parameters for ratio of means for pulsatile PE dose relative to the IR treatment can be at least about 75%, at least about 80%, at least about 85%, at least about 90%, at least about 95%, at least about 97%, and at least about 100%. In another example, the mean $AUC_{0-4}$ and/or the mean $AUC_{4-8}$ of the extended release dosage form can be substantially equivalent and/or meets or exceeds the mean $AUC_{0-4}$ and the mean $AUC_{4-8}$ of the reference formula (two 10 mg immediate release PE doses administered every four hours).

In another example, the mean $C_{max2}$ of the pulsatile dosage form is greater than the mean $C_{max1}$ of the pulsatile dosage form. In another example, the ratio of the mean $C_{max2}$ of the pulsatile dosage form to the mean $C_{max1}$ of the pulsatile dosage form is greater than 125%, in another about example greater than 150%, in another example greater than 165%, in another example greater than about 170%, in another example greater than 200%, in another example greater than 225%, in another example greater than 300%, and in another example greater than 600%. In the ratio of the mean $C_{max2}$ to the mean $C_{max1}$ is from 90% to 300%, in another example from about 100% to about 250%, in another example from about 125% to about 225%, in another example from about 150% to about 200%, and in another example from about 160% to about 180%.

In one example, the mean $C_{4hr}$ for the pulsatile dosage form can meet or exceed the mean $C_{4hr}$ of the systemic exposures relative to an IR reference formula (commercially available, immediate release PE dose taken at 4 hour intervals) while remaining safe and effective. In one example, the mean $C_{4hr}$ for the pulsatile dosage form can be at least two-fold greater than the mean $C_{4hr}$ of the systemic exposures relative to a reference formula, in another example at least four-fold greater, in another example at least eight-fold greater, and in another example at least ten-fold greater. In another example, the upper bound of the 90% confidence interval for ratio of means for pulsatile PE dosage form relative to the IR treatment of the $C_{4hr}$ can be at least about 90%, at least about 100%, at least about 150%, at least about 200%, at least about 250%, at least about 500%, at least about 1000%, at least about 1250%, at least about 1500%, at least about 2000%, and at least about 2500%. In one example, the lower bound of the 90% confidence interval of the $C_{4hr}$ for ratio of means for pulsatile PE dose relative to the IR treatment can be at least about 90%, at least about 100%, at least about 150%, at least about 250%, at least about 300%, at least about 400%, and at least about 500%.

In one example, the mean $C_{8hr}$ for the pulsatile dosage form can meet or exceed the mean $C_{8hr}$ of the systemic exposures relative to an IR reference formula. In one example the mean $C_{8hr}$ for the pulsatile dosage form is from about 100% to about 400% of the mean $C_{8hr}$ of an IR reference formula, in another example from about 110% to about 200%, in another example from about 120% to about 175%, in another example from about 130% to about 160%, and in another example from about 140% to about 150%. In another example, the mean $C_{8hr}$ for the pulsatile dosage form is at least about 90% of the mean $C_{8hr}$ of an IR reference formula, in another example at least about 100%, in another example at least about 105%, in another example at least about 110%, in another example at least about 115%, in another example at least about 120%, in another example at least about 125%, in another example at least about 130%, in another example at least about 135%, in another example at least about 140%, and in another example at least about 145%.

In one example, the mean $C_{4hr}$ for the pulsatile dosage form can meet or exceed the mean $C_{8hr}$ for the pulsatile dosage. In another example, the mean $C_{max2}$ for the pulsatile dosage form can meet or exceed the mean $C_{max1}$ for the pulsatile dosage form.

In another example, the mean $C_{4hr}$ for the pulsatile dosage form is less than the mean $C_{max1}$ for the pulsatile dosage form, for instance the mean $C_{4hr}$ can be at least from about 10% to about 50% of the mean $C_{max1}$, from about 15% to about 45%, from about 20% to about 40%, from about 25% to about 35%, from about 27% to about 30%. In another example, $C_{4hr}$ is less than about 50% of $C_{max1}$, less than about 42%, less than about 40%, less than about 38%, less than about 35%, less than about 32%, less than about 30%.

In another example, mean $C_{8hr}$ for the pulsatile dosage form is less than the mean $C_{max2}$ for the pulsatile dosage form, for instance the mean $C_{4hr}$ can be at least from about 1% to about 20% of the mean $C_{max1}$, from about 2% to about 15%, from about 3% to about 10%, and from about 4% to about 7%. In another example, the mean $C_{8hr}$ for the pulsatile dosage form is less than about 12% of the mean $C_{max2}$ for the pulsatile dosage form, less than about 8%, less than about 7%, less than about 6%, and less than about 5%.

In another example, the mean $AUC_{4-8}$ for the pulsatile dosage form is at least about 60% of the mean $AUC_{0-4}$ for the pulsatile dosage form, at least about 65%, at least about 70%, at least about 72%, at least about 75%, at least about 77%, at least about 85%, at least about 90%, at least about 95%, at least about 100%, at least about 125%, and at least about 150%. In another example, the mean $AUC_{4-8}$ for the pulsatile dosage form is from about 55% to about 100% of the mean $AUC_{0-4}$ for the pulsatile dosage form, from about 60% to about 95%, from about 65% to about 88%, from about 68% to about 86%, from about 74% to about 81%, and from about 76% to about 80%.

In another example the pulsatile dosage form achieves a mean $t_{max}2$ (the time it takes to reach $C_{max2}$) in about 3 hours to about 7 hours, in about 3.5 hours to about 6.8 hours, in about 3.7 hours to about 6.5 hours, in about 4 hours to about 6 hours, and in about 4.5 hours to about 5.5. hours.

In one example, the delayed release form and the immediate release form can contain about the same amount of phenylephrine. In another example, the delayed release form can contain more phenylephrine than the immediate release form. In another example, the delayed release form can contain less phenylephrine than the immediate release form.

As used herein, exceeds bioequivalence limits may include significant increases in one or more pharmacokinetic parameters including $C_{max}$ and/or AUC of unconjugated phenylephrine. For example, exceeds bioequivalence limits can include a greater than 2 fold increase in $C_{max}$ and/or AUC of unconjugated phenylephrine, in another example a greater than 3 fold increase, in another example a greater than 4 fold increase, in another example a greater than 5 fold increase, in another example a greater than 6 fold increase, in another example a greater than 7 fold increase, in another example a greater than 8 fold increase, in another example a greater than 9 fold increase, and in another example a greater than 10 fold increase. In one example, dosage forms that exceed bioequivalence limits can be safe and efficacious.

The dosage form can contain an immediate release dose in any form. In one example the immediate release dose can be coated on immediate release particles. In another example, the immediate release dose is not an immediate release particle. In another example, the immediate release dose can be in a liquid. In another example the immediate release dose can be a liquid and the delayed release particles are suspended in the liquid. In another example, the immediate release dose can be a combination of forms.

In another example, the immediate release dose can be a separate dosage form, for instance a tablet or a liquid and in one example the immediate release dose form is separate and taken concurrently with the extended release particles.

In another example, the immediate release dose can be a granule and/or powder that contains the active and optionally excipients for stability and processing. In the immediate release granules and/or powders, the actives and excipients can be dispersed, possibly approximately evenly dispersed, throughout the granules and/or powders. In one example, the granules and/or powder do not contain a coating. In another example, the granules and/or powder do not contain an active coating. In another example the granules and/or powder contain an active coating containing phenylephrine.

The dosage form can contain immediate release particles or other immediate release forms comprising phenylephrine or salts thereof and delayed release particles comprising phenylephrine or salts thereof. Any pharmaceutically acceptable salt of phenylephrine can be administered. Non-limiting examples of phenylephrine or salts thereof can include phenylephrine hydrochloride, phenylephrine bitartrate, phenylephrine tannate, and combinations thereof. In one example, the dosage form can contain phenylephrine hydrochloride.

In addition to comprising phenylephrine, the dosage forms can contain one or more drug actives in addition to phenylephrine. In one example, the drug actives can be immediate release drug actives, extended release drug actives, and/or delayed release drug actives. In one example, the additional drug active can be formulated as particles.

In one example, the dosage form can be orally administered to a human to temporarily relieve sinus congestion and pressure and/or temporarily relieve nasal congestion due to the common cold, hay fever or other upper respiratory allergies. In one example, the human can be an adults and children 12 years and older. In one example, the human can be an adults and children 16 years and older. In one example, the human can be an adult 18 years and older. In another example, the human can be a child 4 to under 12 years.

In another example, one dose can be administered every eight hours, up to three times per day. In one example, the dosage form can be administered every six hours, in another example every seven hours, in another example every eight hours, in another example every nine hours, in another example every ten hours, and in another example every twelve hours. In one example, the dose can be administered up to four times per day, in another example up to three times per day, in another example up to two times per day, and in another example once per day. In one example, the dosage form can be administered once or twice and a different dosage form can be administered at bedtime.

The dosage forms can be considered safe and can have safety variables, including blood pressure, heart rate, and/or ECG parameters substantially similar or similar to a two sequential doses of immediate release phenylephrine taken four hours apart.

In one example, the additional drug active is a multi-symptom relief (MSR) cold/flu active which can be used to treat one or more cold/flu symptoms. MSR cold/flu actives can be used to treat a variety of cold/flu symptoms including nasal congestion, runny nose, sneezing, headache, dry cough, sore throat, sinus pressure or pain, chest congestion, muscle aches/pains, wet/chesty cough, fever, and combinations thereof. MSR cold/flu actives can include decongestants, expectorants, antihistamines, antitussives, pain relievers, and combinations thereof.

Non-limiting examples of expectorants can include guaifenesin, ambroxol, bromhexine, and combinations thereof.

Non-limiting examples of antihistamines can include chlorpheniramine, desloratadine, levocetirizine, diphenhydramine, doxylamine, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyldiphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, and combinations thereof.

Non-limiting examples of antitussives can include dextromethorphan, menthol, codeine, chlophedianol, levodropropizine, and combinations thereof.

Non-limiting examples of pain relievers can include acetaminophen, ibuprofen, ketoprofen, diclofenac, naproxen and salts thereof, aspirin, and combinations thereof.

In one example, the expectorant can be guaifenesin and in one example the dosage form can contain 200 mg of guaifenesin. In one example, the antihistamine can be chlorpheniramine and in one example the dosage form can contain 125 mg of chlorpheniramine. In one example the antitussive can be selected from the group consisting of dextromethorphan, chlophedianol, and combinations thereof. In one example the dosage form can contains 10 mg of dextromethorphan and in another example the dosage form can contain 12.5 mg chlophedianol. In one example the pain relievers can include acetaminophen, ibuprofen, naproxen, or combinations thereof. In one example the dosage form can contain 325 mg to 500 mg acetaminophen, in another example 200 mg ibuprofen, in another example, 200 mg naproxen, and in another example 220 mg naproxen sodium. In one example, the cold/flu dosage unit can further comprise a stimulant such as caffeine.

In one example, the dosage units can contain one or more MSR cold/flu actives, in another example two or more MSR cold/flu actives, in another example three or more MSR cold/flu actives, and in another example four or more MSR cold/flu actives. In one example, the dosage unit can contain exactly one MSR cold/flu active, in another example exactly two MSR cold/flu actives, in another example exactly three MSR cold/flu actives, and in another example exactly four MSR cold/flu actives. In one example the dosage units can contain acetaminophen, dextromethorpan, and phenylephrine. In another example the dosage units can contain naproxen and/or naproxen sodium, dextromethorpan, and phenylephrine.

Krebs Buffer Dissolution Method

The Krebs Buffer Dissolution Method can be used to approximate the release rate of phenylephrine in the digestive tract, in vitro. Testing is performed using the Type II (paddles) dissolution apparatus, as described in USP <711> (Dec. 1, 2013).

Assemble the apparatus then place 500 mL of 0.1N HCl into each of 6 vessels. Cover the vessels and allow the medium to equilibrate to a temperature of 37±0.5° C. Place one gelatin capsule containing delayed release particles into each vessel and commence dissolution testing. Operate the paddle speed at 50 revolutions per minute (RPM) for two hours. Stainless steel, spring style capsule sinkers that are 23 mm long by 8 mm wide (commercially available as Sotax style sinker, part #CAPWST-23 from QLA, Telford, Pa.) are used to prevent the capsules from floating in the vessels.

After two hours of dissolution in 0.1N HCl, withdraw a 10 mL aliquot of sample from each vessel using separate 10 cc syringes connected to stainless steel cannulae with attached 10 μm filters (available from QLA). Transfer each filtered acid phase sample into separate HPLC vials for analysis.

Then proceed immediately to the Krebs Buffer Stage of dissolution testing. This portion of the method requires a complete media exchange. Carefully transfer the undissolved particles and sinkers from each acid phase vessel to an apparatus containing 1000 mL pH 7.4 Krebs buffer media into each of six vessels. Table 8, below, shows the composition of Krebs buffer. The Krebs buffer is prepared fresh at time of use. The pH of the media in each vessel is adjusted to 7.40±0.05 prior to starting the test using a sparging cannulae connected to a supply of carbon dioxide gas. This gas is sparged directly into the vessels to lower the pH to the target value. The buffer should also be equilibrated to 37±0.5° C. prior to starting the test. Throughout the entire test, gas is sparged into the vessels as needed at low pressure to maintain the pH within 7.40±0.05. The pH level inside the vessel is monitored by a portable pH meter.

TABLE 8

| Buffer Component | Millimolar (mM) | Grams per liter |
|---|---|---|
| Sodium chloride | 118.07 | 6.900 |
| Potassium chloride | 4.69 | 0.350 |
| Magnesium sulfate | 1.18 | 0.142 |
| Calcium chloride dihydrate | 2.52 | 0.370 |
| Potassium phosphate | 1.18 | 0.161 |
| Sodium bicarbonate | 24.00 | 2.016 |

The apparatus is operated at 50 RPM for up to eight hours. A 10 mL aliquot of sample is removed at appropriate intervals (e.g. every 30 minutes) with a separate 10 cc syringe connected to a stainless steel cannula with attached 10 μm filter (available from QLA).

Then use the HPLC-UV Assay, as described herein, is used to determine the percent dissolved values of phenylephrine in each sample aliquot.

HPLC Dissolution Assay

This method is applicable for the determination of phenylephrine in sample aliquots from the Krebs Buffer Dissolution Method. The samples are analyzed by HPLC with UV detection. The HPLC column is an Agilent Zorbax Rapid Resolution, Catalog #HP863953-902, SB-C18, 3.5 μm, 4.6×150 mm First, the stock and working standard solutions are prepared. These solutions should be prepared fresh at time of use.

Standard Solution Preparation

Stock Solution (0.2 mg/mL)
Weigh 40.00±2 mg of Phenylephrine Reference Standard and transfer to a 200 mL volumetric flask. Add approximately 20 mL of water and gently swirl, or sonicate if necessary, to dissolve. Dilute to volume with water and mix well.

Acid Working Standard Solution (0.004 mg/mL)
Dilute stock solution 1:50 by adding 2 mL of stock solution into a 100 mL volumetric flask, and bringing to volume with 0.1N HCl acid dissolution media. Mix well.

pH 7.4 Working Standard Solution (0.01 mg/mL)
Dilute stock solution 1:20 by adding 5 mL of stock into a 100 mL volumetric flask, and bringing to volume with pH 7.4 Krebs buffer media. Mix well.

Set up the HPLC system as per the Chromatic Conditions, in Table 9, below.

TABLE 9

| Gradient Conditions | Time (min) | % A (0.1% TFA) | % B (Acetonitrile) |
|---|---|---|---|
| | 0.0 | 96 | 4 |
| | 3.5 | 96 | 4 |
| | 3.6 | 50 | 50 |
| | 4.5 | 50 | 50 |
| | 4.6 | 96 | 4 |
| | 7.0 | 96 | 4 |
| Run Time: 7 minutes | | Linear Gradient | |
| Column Temperature (° C.) | | 40 | |
| Sample compartment temperature | | Ambient | |
| Flow Rate (mL/min) | | 1.5 | |
| Detector Wavelength (nm) | | 275 | |
| Injection volume (μL) | | 50 | |

When the baseline stabilizes, inject at least one 0.1N HCl blank, followed by at least one injection of the 0.1N HCl working standard solution to equilibrate the system.

Once the system is equilibrated, make 5 injections of the acid working standard solution and evaluate System Suitability Requirements 1-3, below.

Next, inject the acid-phase samples. Inject a bracketing standard at least after every sixth acid-phase sample and after the last acid-phase sample. Evaluate System Suitability Requirement 4, below, for all acid-phase bracketing standard injections made throughout the run. Use the overall average peak area from all acid standard injections made throughout the run to calculate the acid-phase sample results.

After completing the acid-phase sample analysis, continue on to run the buffer-phase analyses. As with the acid-phase analysis, each buffer-phase analysis must be performed with discrete quantitation against the respective pH-matched blank and standards. Begin with at least one injection of the buffer blank solution (pH 7.4 Krebs Buffer dissolution media). Next, make 5 injections of the corresponding pH 7.4 working standard solution followed by the respective sample injections. Make a bracketing buffer standard injection at least every sixth and after the last respective buffer sample. Evaluate System Suitability Criteria 4 for all buffer-phase bracketing standard injections made throughout the run. Then, the average peak area for all for all buffer standard injections is calculated and used in the equations below to calculate the sample results.

System suitability may be calculated after the chromatographic sequence has been run. If the system suitability results fail to meet Requirements 1-3 for the acid working standard solution, then all data (acid and Krebs buffer) must be rejected and the sequence repeated. If a bracketing standard fails to meeting Requirement 4, then the corresponding samples bracketed by that standard must be rejected and the analysis repeated.

System Suitability Reguirements

1. Peak Tailing Factor—the tailing factor must be 2.0 or less for the first acceptable acid standard injection.
2. Peak Area Repeatability—The Relative Standard Deviation (RSD) for the peak area responses must be 2% or less for the first five acceptable acid standard injections.
3. Peak Retention Time Repeatability—The RSD for the peak retention times must be 2% or less for the first five acceptable acid standard injections.
4. Overall Standard Peak Area Repeatability—The overall % RSD of the peak areas for all standard injections made throughout the run (5 initial injections plus bracketing standards) must be 2% or less.

Calculations $$\% \text{ Dissolved (Acid-Phase)} = \frac{\text{Peak Area Sample}}{Avg \text{ Peak Area Working } Std} \times$$
$$\text{Acid Working } Std \text{ } Conc \left(\frac{\text{mg}}{\text{mL}}\right) \times \frac{500 \text{ mL}}{\text{Dose Strength (mg)}} \times 100$$

$$\% \text{ Dissolved (Buffer-Phase)} = \frac{\text{Peak Area Sample}}{Avg \text{ Peak Area Working } Std} \times$$
$$\text{Buffer Working } Std \text{ } Conc \left(\frac{\text{mg}}{\text{mL}}\right) \times \frac{1000 \text{ mL}}{\text{Dose Strength (mg)}} \times 100$$

If active is released during the acid phase, the pH 7.4 buffer phase % dissolved value needs to be corrected to account for active loss during the media exchange. The acid phase portion of the test (sample taken at 2 hours) should have little to no active release. The % dissolved value should be zero. If it is not, then this value needs to be added to all buffer phase results.

Smoothness Test Method

The Smoothness Test Method can be used to determine the circularity of the particles. Circularity is determined by $(4\pi \times ([\text{Area}])/([\text{Perimeter}]^2))$ and ranges from 0 (infinitely elongated polygon) to 1 (perfect circle). Thus, a particle with a rough, coarse, or spiked appearance can have a larger perimeter value as compared to a smooth particle with the same area. Therefore, differences in surface topology can be calculated using the differences in the obtained circularity results.

Using a microscope (Nikon OPTIPHOT-2) and 40× magnification (4× magnifier and 10× eyepiece) and a digital camera (OptixCam Summit OCS-10.0) designed for microscopy, select the field of view that contains the particles to be analyzed. There should be spaces between the particles in the selected field of view.

The image is saved in an acceptable file format, such as JPEG, and opened using ImageJ 1.49v (Image Processing and Analysis in Java) computer software using the "File/Open" menu pointed to the stored file directory.

Next, adjust the settings on ImageJ. Open the threshold settings panel and select the following: method (Default), Color (B&W), and Color Space (HSB).

Figure 9A:
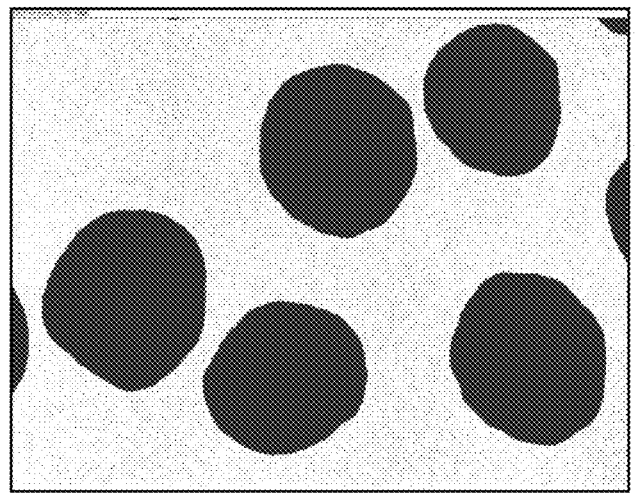
FIGS. 9A and 9B show exemplary images of the field of view used in the Smoothness Test Method.
Figure 9B:
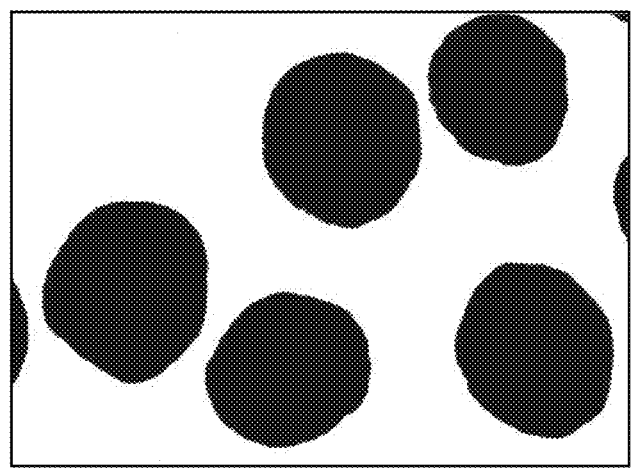

The next step is to tune the white background and black particles to make sure that the images to be studied are completely filled within the outline masks. This is done using the brightness sliders in the software program. Slide the brightness slider so snow appears in the background, as in FIG. 9A. Then, slide the brightness adjustments just until the background becomes white again, without any snow, as in FIG. 9B.

The image is ready for measurement processing. Using the "Set Measurements" menu, assign the measurements t be taken for the image. For this test, "Shape descriptors" must be checked for circularity and roundness measurements. Then, use the "Analyze Particles" command from the "Analyze" menu to select a size filter, to omit any small particles to not be included in measurement. This is done by selecting size (pixel^2): 500-Infinity. In the "Analyze Particles" command, also select display results, clear results, summarize, exclude on edges, and include holes. Exclude on edges will not include any thresholded particles on the edge of the image, only those within full view. Also select Show: "Overlay Outlines" to create new image with analyzed particles highlighted for easy reference. Now, select "OK" to analyze the particles. An image summary report and outline overlay of the original image will be displayed.

Repeat ten times with each population of particles, changing the field of view each time and calculate the mean circularity.

Tables 10-14, below, show the treatments used in Examples 1-4.

TABLE 10

Example 1 Treatments

| | Treatment 1 | Treatment 2 | Treatment 3 | Treatment 4 |
|---|---|---|---|---|
| PE Coated Cellets | 700 g | 700 g | 700 g | 700 g |
| Eudragit ® FS 30D[1] | 1020.9 g | 1020.9 g | 1084.7 g | 1212.0 g |
| Eudragit ® L30D-55[2] | 180.6 g | 180.6 g | 120.8 g | 0 g |
| Polysorbate 80 | 3.5 g | 3.5 g | 3.6 g | 3.6 g |
| Triethyl Citrate | 20.7 g | 20.7 g | 19.9 g | 18.0 g |
| Glycerol Monostearate | 15.0 g | 15.0 g | 14.9 g | 14.4 g |
| Purified Water | 758.8 g | 758.8 g | 756.4 g | 752.0 g |
| Total Solution | 1999.5 g | 1999.5 g | 2000.3 g | 2000.0 g |
| Grams Sprayed | 1028.7 g | 1732.3 g | 1043.7 g | 1029.2 g |
| Target Batch Size | 905.6 g | 1046.2 g | 908.7 g | 905.6 g |
| Wt % Increase | 29.4% | 49.5% | 29.8% | 29.4% |
| Wt % of pH Sensitive Coating | 22.7% | 33.1% | 23.0% | 22.7% |

[1,2] Available from Evonik Industries (Darmstadt, Germany)

TABLE 11

Examples 2 and 4 Treatments C, A, and D

| | 10 mg IR/3 mg delayed release (50% pH coating) capsules | | 10 mg IR/5 mg delayed release (40% pH coating) capsules | | 10 mg IR/5 mg delayed release (50% pH coating) capsules | |
|---|---|---|---|---|---|---|
| | Treatment | | | | | |
| | C | | A | | D | |
| | % | mg | % | mg | % | mg |
| Delayed Release Particle | | | | | | |
| Phenylephrine HCl | 2.62 | 3 | 4.38 | 5 | 4.07 | 5 |
| Cellets 500 (microcrystalline cellulose core) | 55.55 | 63.67 | 58.23 | 66.43 | 54.1 | 66.43 |
| Kollicoat ® IR (solids) | 3.81 | 4.36 | 4.1 | 4.67 | 3.81 | 4.67 |
| Talc | 1.9 | 2.18 | 2.05 | 2.34 | 1.9 | 2.34 |
| Eugradit FS30D | 31.94 | 36.6 | 27.5 | 31.38 | 31.94 | 39.22 |
| PlasACRYL ™ T20 | 3.19 | 3.66 | 2.75 | 3.14 | 3.19 | 3.92 |
| (Triethyl Citrate) | 1.68 | 1.92 | 1.44 | 1.65 | 1.68 | 2.06 |
| (Glycerol monostearate) | 1.34 | 1.54 | 1.15 | 1.32 | 1.34 | 1.65 |
| (Polysorbate 80) | 0.18 | 0.2 | .15 | .18 | .18 | 0.22 |
| Aerosil ® 200 (SiO2) | 0.99 | 1.13 | 0.99 | 1.13 | 0.99 | 1.22 |
| Immediate Release Particle | | | | | | |
| Phenylephrine HCl | 8.66 | 10 | 8.66 | 10 | 8.66 | 10 |
| Cellets 500 (microcrystalline cellulose core) | 81.51 | 94.17 | 81.51 | 94.17 | 81.51 | 94.17 |
| Kollicoat ® IR (solids) | 5.9 | 6.81 | 5.9 | 6.81 | 5.9 | 6.81 |

TABLE 11-continued

Examples 2 and 4 Treatments C, A, and D

|  | 10 mg IR/3 mg delayed release (50% pH coating) capsules Treatment C | | 10 mg IR/5 mg delayed release (40% pH coating) capsules Treatment A | | 10 mg IR/5 mg delayed release (50% pH coating) capsules Treatment D | |
|---|---|---|---|---|---|---|
|  | % | mg | % | mg | % | mg |
| Talc | 2.95 | 3.41 | 2.95 | 3.41 | 2.95 | 3.41 |
| Aerosil ® 200 (SiO2) | 0.99 | 1.14 | 0.99 | 1.14 | 0.99 | 1.14 |

TABLE 12

Examples 2 and 4 Treatments F, B, and E

|  | 10 mg IR/5 mg delayed release (60% pH coating) capsules Treatment F | | 10 mg IR/7 mg delayed release (40% pH coating) capsules Treatment B | | 10 mg IR/7 mg delayed release (50% pH coating) capsules Treatment E | |
|---|---|---|---|---|---|---|
|  | % | mg | % | mg | % | mg |
| Delayed Release Particle | | | | | | |
| Phenylephrine HCl | 3.8 | 5 | 6.01 | 7 | 5.58 | 7 |
| Cellets 500 (microcrystalline cellulose core) | 50.51 | 66.43 | 56.6 | 65.92 | 52.58 | 65.92 |
| Kollicoat ® IR (solids) | 3.55 | 4.67 | 4.1 | 4.77 | 3.81 | 4.77 |
| Talc | 1.78 | 2.34 | 2.05 | 2.39 | 1.9 | 2.39 |
| Eugradit FS30D | 35.79 | 47.06 | 27.5 | 32.03 | 31.94 | 40.04 |
| PlasACRYL ™ T20 | 3.58 | 4.71 | 2.75 | 3.2 | 3.19 | 4 |
| (Triethyl Citrate) | 1.88 | 2.47 | 1.44 | 1.68 | 1.68 | 2.1 |
| (Glycerol monostearate) | 1.5 | 1.97 | 1.15 | 1.34 | 1.34 | 1.68 |
| (Polysorbate 80) | 0.2 | 0.26 | .15 | .18 | .18 | 0.22 |
| Aerosil ® 200 (SiO2) | 0.99 | 1.3 | 0.99 | 1.15 | 0.99 | 1.24 |
| Immediate Release Particle | | | | | | |
| Phenylephrine HCl | 8.66 | 10 | 8.66 | 10 | 8.66 | 10 |
| Cellets 500 (microcrystalline cellulose core) | 81.51 | 94.17 | 81.51 | 94.17 | 81.51 | 94.17 |
| Kollicoat ® IR (solids) | 5.9 | 6.81 | 5.9 | 6.81 | 5.9 | 6.81 |
| Talc | 2.95 | 3.41 | 2.95 | 3.41 | 2.95 | 3.41 |
| Aerosil ® 200 (SiO2) | 0.99 | 1.14 | 0.99 | 1.14 | 0.99 | 1.14 |

TABLE 13

Example 3 Treatments A and B

|  | 10 mg IR/10 mg delayed release (45% pH Coating) capsules Treatment A | | 10 mg IR/15 mg delayed release (45% pH Coating) capsules Treatment B | |
|---|---|---|---|---|
|  | % | mg | % | mg |
| Delayed Release Fill | | | | |
| Phenylephrine HCl | 7.91 | 10.00 | 11.11 | 15.00 |
| Cellets 500 (microcrystalline cellulose core) | 52.02 | 65.76 | 48.82 | 65.91 |
| Kollicoat IR (solids) | 4.20 | 5.30 | 4.20 | 5.66 |
| Talc | 2.10 | 2.65 | 2.10 | 2.83 |
| Eugradit FS30D | 29.80 | 37.67 | 29.80 | 40.23 |
| PlasACRYL T20 | 2.98 | 3.77 | 2.98 | 4.02 |
| (Triethyl Citrate) | 1.56 | 1.98 | 1.56 | 2.11 |
| (Glycerol monostearate) | 1.25 | 1.58 | 1.25 | 1.69 |
| (Polysorbate 80) | 0.17 | 0.21 | 0.17 | 0.23 |
| Aerosil 200 (SiO2) | 0.99 | 1.25 | 0.99 | 1.34 |

TABLE 13-continued

Example 3 Treatments A and B

| | 10 mg IR/10 mg delayed release (45% pH Coating) capsules | | 10 mg IR/15 mg delayed release (45% pH Coating) capsules | |
|---|---|---|---|---|
| | Treatment | | | |
| | A | | B | |
| | % | mg | % | mg |
| Immediate Release Fill | | | | |
| Phenylephrine HCl | 8.60 | 10.00 | 8.60 | 10.00 |
| Cellets 500 (microcrystalline cellulose core) | 81.00 | 94.17 | 81.00 | 94.17 |
| Kollicoat IR (solids) | 6.27 | 7.29 | 6.27 | 7.29 |
| Talc | 3.14 | 3.65 | 3.14 | 3.65 |
| Aerosil 200 (SiO2) | 0.99 | 1.15 | 0.99 | 1.15 |

TABLE 14

Example 3 Treatments C and D

| | 10 mg IR/20 mg delayed release (45% pH Coating) capsules | | 15 mg IR/15 mg delayed release (45% pH Coating) capsules | |
|---|---|---|---|---|
| | Treatment | | | |
| | C | | D | |
| | % | mg | % | mg |
| Delayed Release Fill | | | | |
| Phenylephrine HCl | 11.11 | 20.00 | 11.11 | 15.00 |
| Cellets 500 (microcrystalline cellulose core) | 48.82 | 87.87 | 48.82 | 65.91 |
| Kollicoat IR (solids) | 4.20 | 7.55 | 4.20 | 5.66 |
| Talc | 2.10 | 3.78 | 2.10 | 2.83 |
| Eugradit FS30D | 29.80 | 53.64 | 29.80 | 40.23 |
| PlasACRYL T20 | 2.98 | 5.36 | 2.98 | 4.02 |
| (Triethyl Citrate) | 1.56 | 2.81 | 1.56 | 2.11 |
| (Glycerol monostearate) | 1.25 | 2.25 | 1.25 | 1.69 |
| (Polysorbate 80) | 0.17 | 0.30 | 0.17 | 0.23 |
| Aerosil 200 (SiO2) | 0.99 | 1.78 | 0.99 | 1.34 |
| Immediate Release Fill | | | | |
| Phenylephrine HCl | 8.60 | 10.00 | 11.83 | 15.00 |
| Cellets 500 (microcrystalline cellulose core) | 81.00 | 94.17 | 77.77 | 98.64 |
| Kollicoat IR (solids) | 6.27 | 7.29 | 6.27 | 7.95 |
| Talc | 3.14 | 3.65 | 3.14 | 3.98 |
| Aerosil 200 (SiO2) | 0.99 | 1.15 | 0.99 | 1.26 |

Examples 1-4 were made as follows. First, 7000 grams (g) of Cellets® 500 (available from Glatt® Air Techniques Inc., Ramsey, New Jersey) were spray coated with an aqueous solution containing 1235.0 g phenylephrine hydrochloride dissolved in 11,115 g of purified water and then dried in a GPCG-5 fluid bed column with 9 inch Wurster Insert (available from Glatt® Air Techniques, Ramsey, N.J.). The fluid bed column was attached to a calibrated pump set at a constant rate of 20-60 grams per minute. The Cellets® with the aqueous coating were then dried in the fluid bed column for five minutes at 20 cubic feet per minute (CFM) at a temperature between 35 degrees Celsius (° C.) and 45° C. to form the phenylephrine hydrochloride (PE-HCl) coated Cellets®.

In a separate container, polysorbate 80, triethylcitrate, and glycerolmonostearate were combined in 540 g of purified water. The polysorbate 80, triethylcitrate, and glycerolmonostearate mixture was heated by a hot plate between 70° C. and 80° C. and stirred with a propeller mixer. After the ingredients were dissolved, the solution was cooled to room temperature, which was less than 33° C., and purified water was added to produce approximately 2000 g of solution. In Example 1, 212 g of purified water was added so the total solution weighed 2000 g. Then the Eudragit® FS-30D was added to the solution (available from Evonik Industries, Darmstadt, Germany) and was stirred with a propeller mixer for 60 min to form Dispersion 1.

In Example 1, Dispersion 1 was sprayed onto 700 g of the PE-HCl coated Cellets® using a calibrated pump sprayer attached to a fluid bed column set to a rate between 20-60 grams per min. The spray coating was performed within the GPCG-5 fluid bed column with a 6" Wurster insert at 45±10° C. 905.6 g of coated particles were obtained after drying for 5 min in the same fluid bed column with an air inlet temperature of 45±10° C.

For Examples 2, 3, and 4 the process of dissolving the polysorbate 80, triethylcitrate, and glycerolmonosterate from above was repeated and then the Eudragit® L30D-55 was added as described above to form Dispersion 2.

In Examples 2, 3, and 4, Dispersion 1 and 2 were combined into a single container and stirred at room temperature for 45 minutes using a propeller mixer. The final volume was adjusted with purified water to produce approximately 2000 g of the combined total solution. The combined total solution was then screened through a US 60 mesh screen into a clean container and stored at room temperature and was stirred continuously until use. The combined total solution was used within 48 hours after it was screened.

Next, the combined total solution was sprayed onto 700 g of the PE-HCl coated Cellets® and dried for five minutes as described above. 900-1050 grams, depending on the weight percent of the coating, of coated particles were obtained after drying for five minutes as described above.

Examples 5-15 include both immediate release and delayed release particles. As a first step, drug layered particles were produced using a batch size of 7000g of Cellets® 500. PE-HCl spray solutions were prepared in an appropriately sized vessel with mixing element via dissolving PE-HCl in water to produce a 22.5% concentrated solution. Depending on the example, particles were drug layered in a GPCG-5 fluid bed with 9" Wurster insert to yield particles having a final PE-HCl concentration of 4.5%, 7.0%, 9.6%, 13.2%, and 18.54%. The process conditions for drug layering included a 55° C. inlet air temperature, 40° C. product temperature, 150 CFM air flow rate, and ramping to a 26g/min spray rate.

After a one minute drying step, the drug layered particles from examples 5-11 are then seal coated with a coating spray of 15% Kollicoat® IR and 7.5% talc to a weight gain of 7% based on the Kollicoat® IR polymer. The spray composition is prepared as follows: 59% of the total water was added to an appropriate sized vessel with a propeller mixer. Kollicoat® IR was added while mixing for a minimum of 15 minutes. In a separate container, the remaining water is added and set-up with a high shear mixer. The talc was added and mixed to form a dispersion for a minimum of 5 minutes. The talc dispersion was then added to the Kollicoat® mixture and mixed for at least 10 minutes with the propeller mixer. The Wurster process conditions in the same equipment included a 52° C. inlet air temperature, 42° C. product temperature, 180 CFM air flow rate, and ramping to a 17 g/min spray rate. The seal coated particles were then dried for 5 minutes before discharging or further processing.

Some of the 9.6% PE seal coated particles were topcoated with a 5% Aerosil® 200 suspension to a 1% wt. gain using process conditions in the same equipment having a 53° C. inlet air temperature, 170 CFM air flow rate, and ramping to a 20 g/min spray rate. The top coated particles were dried for 5 minutes. The 5% Aerosil® 200 suspension was prepared by adding water to an appropriate sized container that includes a propeller mixer. This version is for the immediate release particle.

The other lots were enteric coated to specified wt. gain of enteric polymer using the GPCG-5 fluid bed with 7" wurster at a batch size of 2 kg of the seal coated particles (vide supra). The enteric coated dispersion is made as follows: Water was added to PlasACRYL™ T200 and mixed for 10 minutes minimum in an appropriate sized mixing vessel with tri-blade mixer. While mixing, the Eudragit® FS3OD polymer was added and mixed for 5 minutes minimum to make a uniform dispersion. The mixture was passed through a #60 US standard sieve to remove any clumps present. The process conditions used include a 39° C. inlet air temperature, 30° C. product temperature, 160 CFM air flow rate, and ramping to a 22 g/min spray rate. The enteric coated particles were dried for one minute.

The enteric coated particles were then top coated with a 5% Aerosil® 200 suspension (made as above) to a 1% wt. gain using process conditions in the same equipment having a 39° C. inlet air temperature, 30° C. product temperature, 160 CFM air flow rate, and ramping to a 18 g/min spray rate. The top coated particles were then dried for 5 minutes. This version is for the delayed release particle.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Accordingly, all numerical values are understood to be modified by the term "about." Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for temporarily relieving sinus congestion and pressure comprising administering to a human a dose of a multi-particle pulsatile oral dosage form comprising:
    a. an immediate release form comprising about 10 mg phenylephrine hydrochloride; and
    b. a plurality of delayed release particles wherein each delayed release particle comprises:
        i. a core wherein at least about 85% of the cores comprise a diameter from about 500 μm to about 710 μm;
        ii. a phenylephrine coating comprising phenylephrine hydrochloride;
        iii. a pH sensitive coating comprising an acrylate copolymer selected from the group consisting of methylmethacrylate esters copolymerized with methacrylic acid, acrylic acid and esters copolymerized with methacrylic acid and esters, ammonio-containing acrylate copolymers, and combinations thereof;
            wherein the pH sensitive coating is from 40 μm to about 80 μm thick;
            wherein the plurality of delayed release particles comprise about 10 mg phenylephrine hydrochloride.

2. The method of claim 1 wherein the pH sensitive coating is from about 50 μm to about 70 μm thick.

3. The method of claim 1 wherein the pH sensitive coating comprises poly(methyl acrylate-co-methyl methacrylate-co-methacrylic acid) 7:3:1 polymer.

4. The method of claim 1 wherein the pulsatile dosage form comprises a Cmax2, an $AUC_{0-4}$, and an $AUC_{4-8}$, wherein the Cmax2, the $AUC_{0-4}$, and the $AUC_{4-8}$ for the pulsatile dosage form meets or exceeds systemic exposures relative to two sequential doses of an immediate release phenylephrine taken four hours apart.

5. The method of claim 1 wherein the dose can be readministered every eight hours, up to three times per day, if symptoms persist.

6. A method for temporarily relieving sinus congestion and pressure comprising administering to a human a dose of a multi-particle pulsatile oral dosage form comprising:
    a. an immediate release form comprising about 10 mg phenylephrine hydrochloride; and
    b. a plurality of delayed release particles wherein each delayed release particle comprises:
        i. a core;
        ii. a phenylephrine coating comprising phenylephrine hydrochloride;
        iii. a pH sensitive coating wherein the pH sensitive coating comprises an enteric coating;
            wherein the pH sensitive coating is from 40 μm to about 80 μm thick;
            wherein the plurality of delayed release particles comprise from about 7 mg to about 15 mg phenylephrine hydrochloride;
            wherein the pulsatile dosage form comprises a $C_{max2}$ and an $AUC_{4-8}$ wherein an upper bound of a 90% confidence interval for a ratio of means for the $C_{max}2$ and the $AUC_{4-8}$ of the pulsatile dosage form relative to two sequential doses of an immediate release phenylephrine taken four hours apart is at least 85%.

7. The method of claim 6 wherein the pH sensitive coating comprises one or more polymers with a weight average molecular weight from about 225,000 g/mol to about 350,000 g/mol.

8. The method of claim 6 wherein the core is substantially free of phenylephrine.

9. The method of claim 8 wherein at least about 85% of the cores comprise a diameter from about 500 μm to about 710 μm.

10. The method of claim 9 wherein at least one delayed release particle comprises a mean circularity from about 0.7 to about 1 as determined by the Smoothness Test Method.

11. The method of claim 6 wherein the pulsatile dosage form further comprises a $C_{max1}$ and wherein a ratio of a mean $C_{max2}$ to a mean $C_{max1}$ is from about 125% to about 225%.

12. The method of claim 6 wherein the pulsatile dosage form further comprises a $C_{8hr}$ wherein a mean $C_{8hr}$ is from about 120% to about 175% of a mean $C_{8hr}$ of two sequential doses of an immediate release phenylephrine taken four hours apart.

13. The method of claim 6 wherein the pulsatile dosage form further comprises a $C_{8hr}$ and wherein a mean $C_{8hr}$ for the pulsatile dosage form meets or exceed a mean $C_{8hr}$ of the systemic exposures relative to two sequential doses of an immediate release phenylephrine taken four hours apart.

14. A method for temporarily relieving sinus congestion and pressure comprising administering to a human a dose of a multi-particle pulsatile oral dosage form comprising:
   a. an immediate release form comprising phenylephrine hydrochloride; and
   b. a plurality of delayed release particles wherein each delayed release particle comprises:
      i. a core;
      ii. a phenylephrine coating comprising phenylephrine hydrochloride;
      iii. a pH sensitive coating wherein the pH sensitive coating is degradable at a pH from about 6 to about 8;
      wherein the plurality of delayed release particles comprise from about 7 mg to about 20 mg phenylephrine hydrochloride;
   wherein the ratio of the amount of phenylephrine in the immediate release form to the amount of phenylephrine in the delayed release form is from about 1.5:1 to about 1:1.5;
   wherein the pulsatile dosage form comprises an $AUC_{0-4}$ and an $AUC_{4-8}$ wherein a mean $AUC_{0-4}$ and a mean $AUC_{4-8}$ of the pulsatile dosage form meets or exceeds a mean $AUC_{0-4}$ and a mean $AUC_{4-8}$ of two sequential doses of an immediate release phenylephrine taken four hours apart.

15. The method of claim 14 wherein the human's heart rate and blood pressure after administering the dosage form and for an entire dosing interval is substantially similar to two sequential doses of immediate release phenylephrine taken four hours apart.

16. The method of claim 14 wherein the immediate release form comprises about 10 mg phenylephrine hydrochloride and wherein the delayed release form comprises about 10 mg phenylephrine hydrochloride.

17. The method of claim 14 wherein the delayed release particle is from about 400 μm to about 800 μm in its longest dimension.

18. The method of claim 14 wherein the pulsatile dosage form comprises a $C_{4hr}$ and wherein a mean $C_{4hr}$ for the pulsatile dosage form can meet or exceed a mean $C_{4hr}$ of two sequential doses of an immediate release phenylephrine taken four hours apart.

* * * * *